United States Patent
Cho et al.

(10) Patent No.: US 10,035,830 B2
(45) Date of Patent: Jul. 31, 2018

(54) METHOD FOR TREATMENT OF GM1 GANGLIOSIDOSIS

(71) Applicant: Korea Research Institute of Bioscience and Biotechnology, Daejeon (KR)

(72) Inventors: Yee Sook Cho, Daejeon (KR); Mi Young Son, Daejeon (KR); Jae Eun Kwak, Daejeon (KR); Binna Seol, Daejeon (KR); Hye Jin Jeon, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 14/820,348

(22) Filed: Aug. 6, 2015

(65) Prior Publication Data
US 2016/0068580 A1    Mar. 10, 2016

Related U.S. Application Data

(63) Continuation of application No. PCT/KR2014/011207, filed on Nov. 20, 2014.

(30) Foreign Application Priority Data

Sep. 5, 2014   (KR) .......................... 10-2014-0118659
Nov. 20, 2014  (KR) .......................... 10-2014-0162438

(51) Int. Cl.
| | |
|---|---|
| *C07K 14/47* | (2006.01) |
| *A61K 38/55* | (2006.01) |
| *C12N 5/0793* | (2010.01) |
| *C12N 5/077* | (2010.01) |
| *C12N 5/074* | (2010.01) |
| *C07K 5/02* | (2006.01) |
| *C07K 5/087* | (2006.01) |
| *G01N 33/50* | (2006.01) |

(52) U.S. Cl.
CPC .......... *C07K 14/4703* (2013.01); *A61K 38/55* (2013.01); *C07K 5/0202* (2013.01); *C07K 5/0812* (2013.01); *C12N 5/0619* (2013.01); *C12N 5/0656* (2013.01); *C12N 5/0696* (2013.01); *G01N 33/5023* (2013.01); *C12N 2501/2301* (2013.01); *C12N 2501/602* (2013.01); *C12N 2501/603* (2013.01); *C12N 2501/604* (2013.01); *C12N 2501/606* (2013.01); *C12N 2501/70* (2013.01); *C12N 2501/999* (2013.01); *C12N 2506/1307* (2013.01); *C12N 2506/45* (2013.01); *C12N 2510/00* (2013.01)

(58) Field of Classification Search
None
See application file for complete search history.

(56) References Cited

U.S. PATENT DOCUMENTS

| | | |
|---|---|---|
| 2008/0213893 A1 | 9/2008 | Klassen et al. |
| 2013/0023488 A1 | 1/2013 | Wu |
| 2013/0261067 A1 | 10/2013 | Ragaglia et al. |

FOREIGN PATENT DOCUMENTS

| | | |
|---|---|---|
| JP | 2013-011621 | 1/2013 |
| WO | WO 2003/022797 A1 | 3/2003 |
| WO | WO 2009/049421 A1 | 4/2009 |
| WO | WO 2011/028795 A2 | 3/2011 |
| WO | WO 2015/083736 A1 | 6/2015 |

OTHER PUBLICATIONS

Armstrong-Javors et al. Child Neurology: Exaggerated dermal melanocytosis in a hypotonic infant: A harbinger of GM1 gangliosidosis. Neurology 2014;83;e166-e168.*
L'homme et al. Unsaturated fatty acids prevent activation of NLRP3 inflammasome in human monocytes/macrophages. J. Lipid Res. 2013. 54: 2998-3008.*
Jeyakumar et al. Central nervous system inflammation is a hallmark of pathogenesis in mouse models of GM1 and GM2 gangliosidosis. Brain (2003), 126, 974-987.*
National Tay-Sachs & Allied Disease Association Web Site. GM1 Gangliosidosis-1. https://www.ntsad.org/index.php/the-diseases/gm-1.*
Jeyakumar et al. Storage solutions: treating lysosomal disorders of the brain. Nat Rev Neurosci. Sep. 2005;6(9):713-25.*
Gammelsrud et al. Enniatin B-induced cell death and inflammatory responses in RAW 267.4 murine macrophages. Toxicology and Applied Pharmacology 261 (2012) 74-87. (Year: 2012).*

(Continued)

*Primary Examiner* — Marcela M Cordero Garcia
*Assistant Examiner* — Jia-Hai Lee
(74) *Attorney, Agent, or Firm* — Klarquist Sparkman, LLP

(57) ABSTRACT

The present invention relates to a method for preparing a GM1 gangliosidosis human cell model based on induced pluripotent stem cells (iPSCs) and iPSCs originated neural progenitor cells, and a use of the GM1 model above for the development of a GM1 gangliosidosis treating agent. The iPSCs originated from GM1 patient fibroblasts can be differentiated into neural progenitor cells (NPCs) and neurosphere cells that can emulate the characteristics shown in GM1 patient, so that the said cells can be efficiently used for the investigation of intracellular GM1 symptoms such as the GM1 gangliosidosis and lysosome accumulation and the gene expression pattern change. So, the GM1 cell model of the present invention can be efficiently used for the study of GM1 development mechanism and the study for the development of a therapeutic agent for the disease. The present inventors also established the inflammasome inhibitor rhIL1RA or Z-YVAD-FMK by using the above GM1 cell model and further confirmed that it can be efficiently used as a relieving/treating agent of GM1 gangliosidosis.

6 Claims, 34 Drawing Sheets

(56) References Cited

OTHER PUBLICATIONS

Terada et al. Involvement of Cathepsin B in the Processing and Secretion of Interleukin-1b in Chromogranin A-Stimulated Microglia. GLIA 58:114-124 (2010). (Year: 2010).*

Email communication for interview discussion of unexpected result sent by Attorney. (Year: 2018).*

Lemonnier et al. "Modeling neuronal defects associated with a lysosomal disorder using patient-derived induced pluripotent stem cells," *Human Molecular Genetics* 20(18):3653-3666 (2011).

Chen et al. "Single cell analysis reveals phenotypically distinct sub-populations in putative endothelial cells," *Journal of the American College of Surgeons* 215(3):593-594 (2012).

Tiscornia et al. "Neuronopathic Gaucher's disease: induced pluripotent stem cells for disease modeling and testing chaperone activity of small compounds," *Human Molecular Genetics* 22(4):633-645 (2013).

Son et al. "A novel human model of the neurodegenerative disease GM1 gangliosidosis using induced pluripotent stem cells demonstrates inflammasome activation," *Journal of Pathology* 237:98-110 (2015).

Ryu et al., "Ganglioside GM1 influences the proliferation rate of mouse induced pluripotent stem cells," *BMB Reports* 45:713-718, 2012.

Matsuda et al., "β-Galactosidase-deficient mouse as an animal model for $G_{M1}$-gangliosidosis," *Glycoconjugate Journal* 14:729-736, 1997.

Okumiya et al., "Imbalance substrate specificity of mutant (3-galactosidase in patients with Morquio B disease," Molecular Genetics and Metabolism 78: 51-58 (2003).

* cited by examiner

[Figure 1]
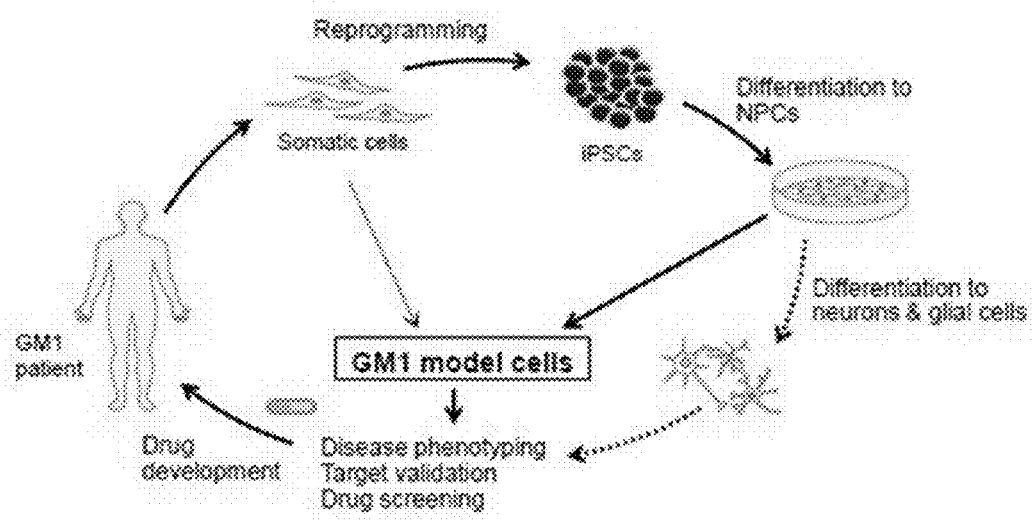

[Figure 5]
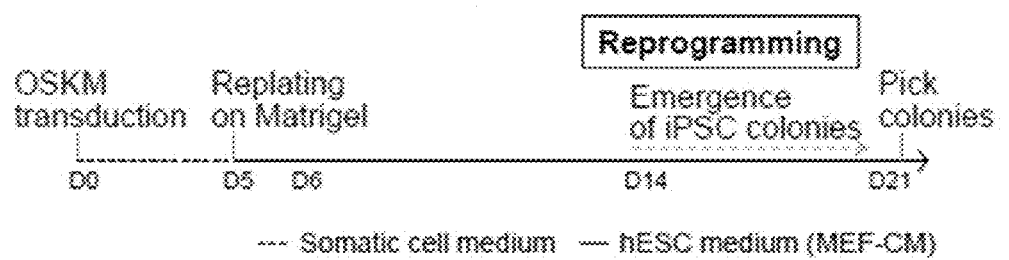

[Figure 6]
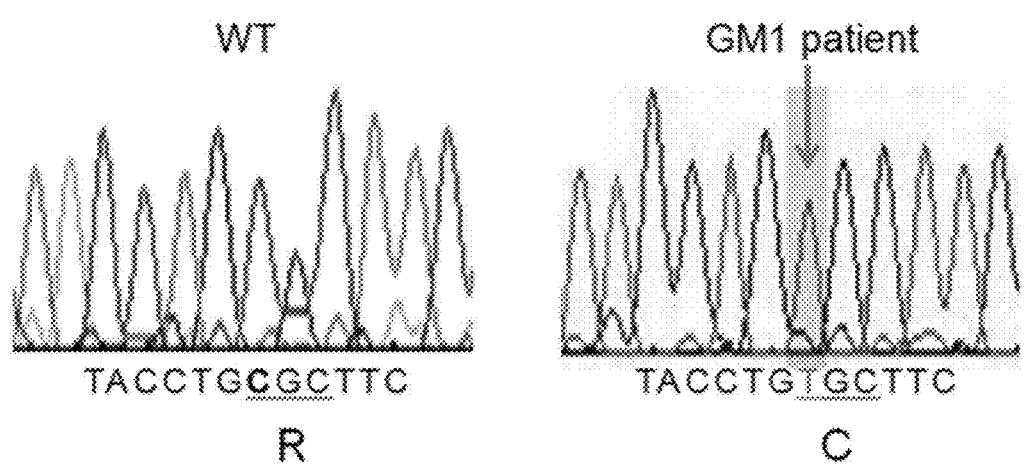
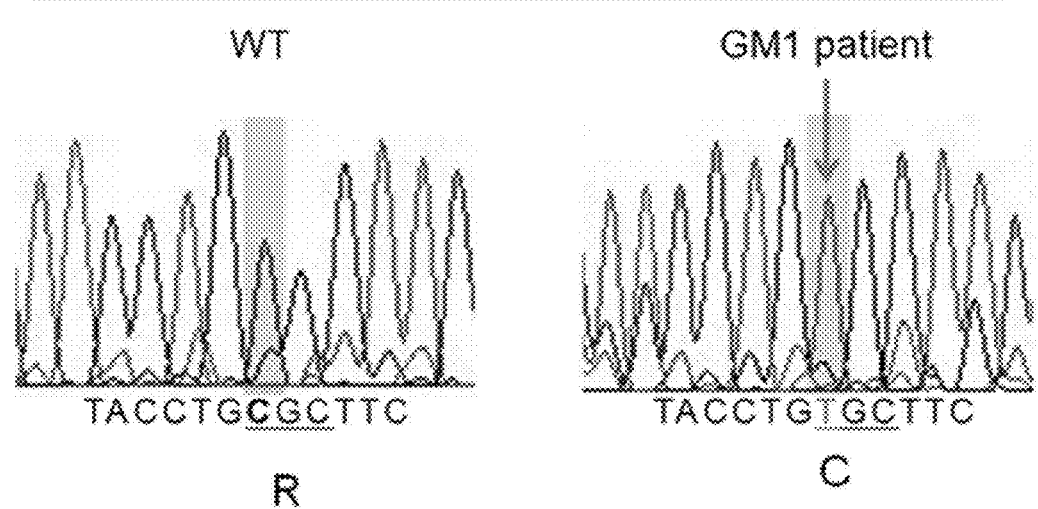

FIG. 7A
FIG. 7B
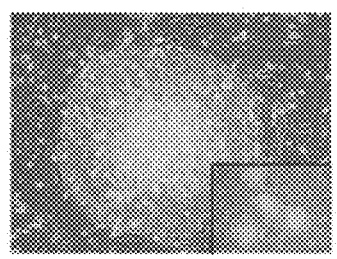
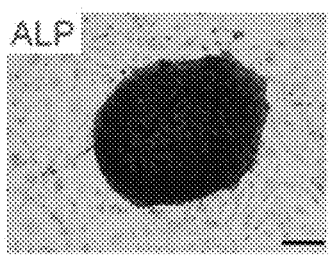
FIG. 7C
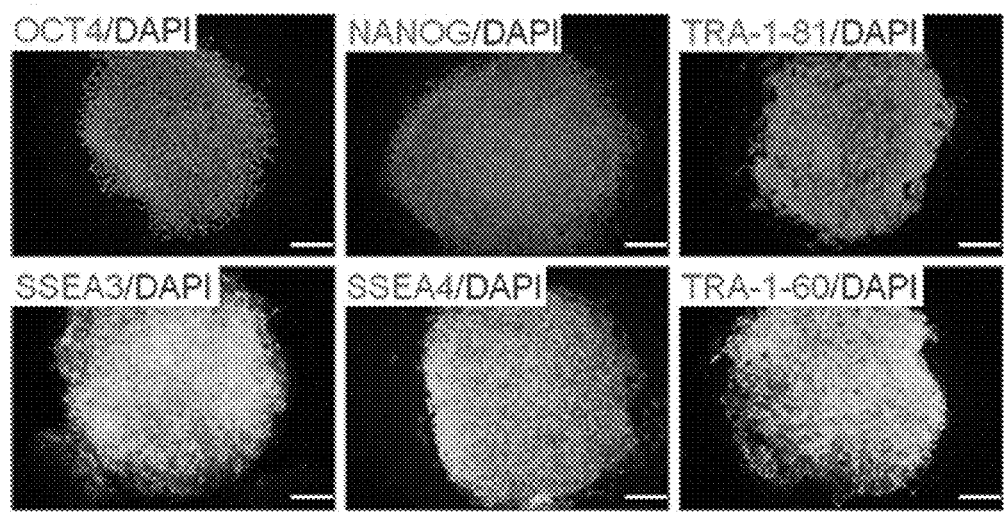

[Figure 8]

| Locus/Clone | H9 hESCs | | GM02439 GM1-fibroblasts | | GM02439 GM1-iPSCs | |
|---|---|---|---|---|---|---|
| D8S1179 | 8 | 14 | 13 | 15 | 13 | 15 |
| D21S11 | 30 | 30 | 30.2 | 32.2 | 30.2 | 32.2 |
| D7S820 | 9 | 11 | 8 | 9 | 8 | 9 |
| CSF1PO | 11 | 11 | 11 | 11 | 11 | 11 |
| D3S1358 | 13 | 16 | 13 | 16 | 13 | 16 |
| TH01 | 9.3 | 9.3 | 6 | 7 | 6 | 7 |
| D13S317 | 9 | 9 | 8 | 10 | 8 | 10 |
| D16S539 | 12 | 13 | 12 | 13 | 12 | 13 |
| D2S1338 | 18 | 24 | 19 | 22 | 19 | 22 |
| D19S433 | 12 | 15 | 13 | 14.2 | 13 | 14.2 |
| vWA | 17 | 17 | 17 | 18 | 17 | 18 |
| TPOX | 10 | 10 | 8 | 8 | 8 | 8 |
| D18S51 | 12.3 | 13 | 12 | 19 | 12 | 19 |
| D5S818 | 11 | 12 | 12 | 13 | 12 | 13 |
| FGA | 26 | 28 | 19 | 21 | 19 | 21 |
| Gender | XX | | XY | | XY | |

[Figure 9]
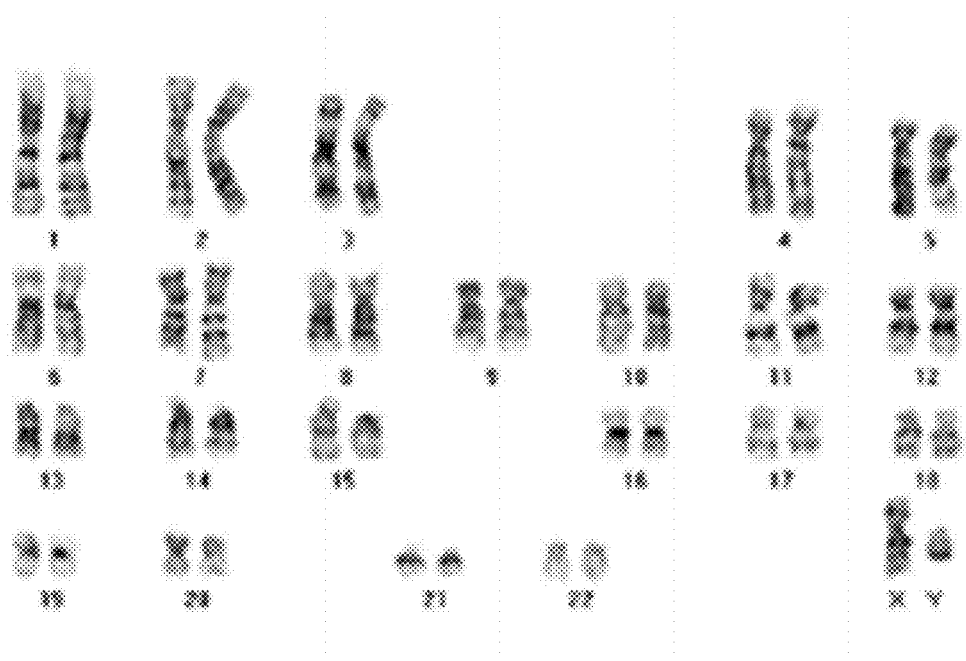

[Figure 10]
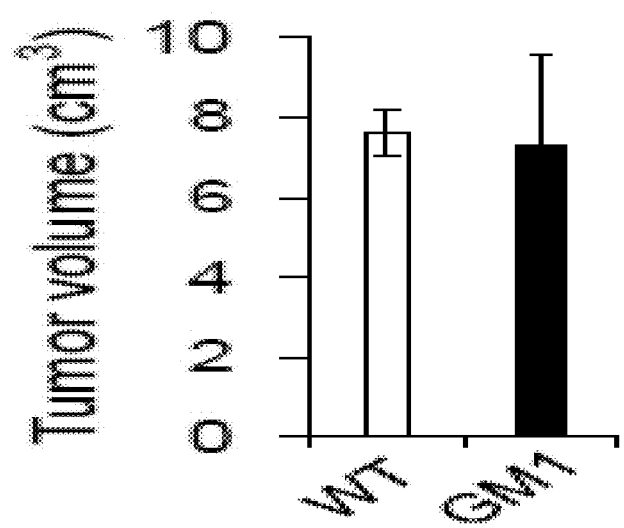

[Figure 11]
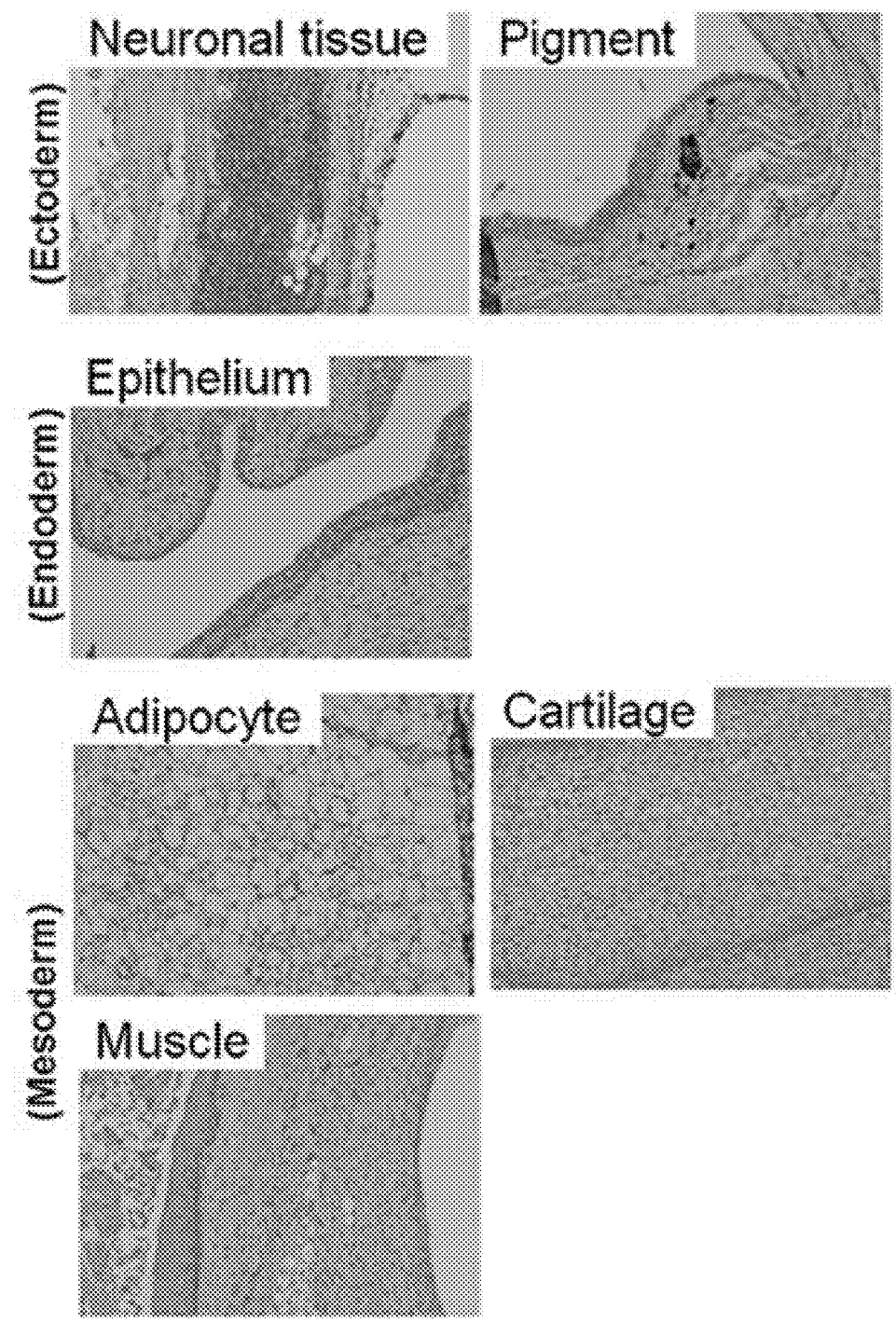

[Figure 12]
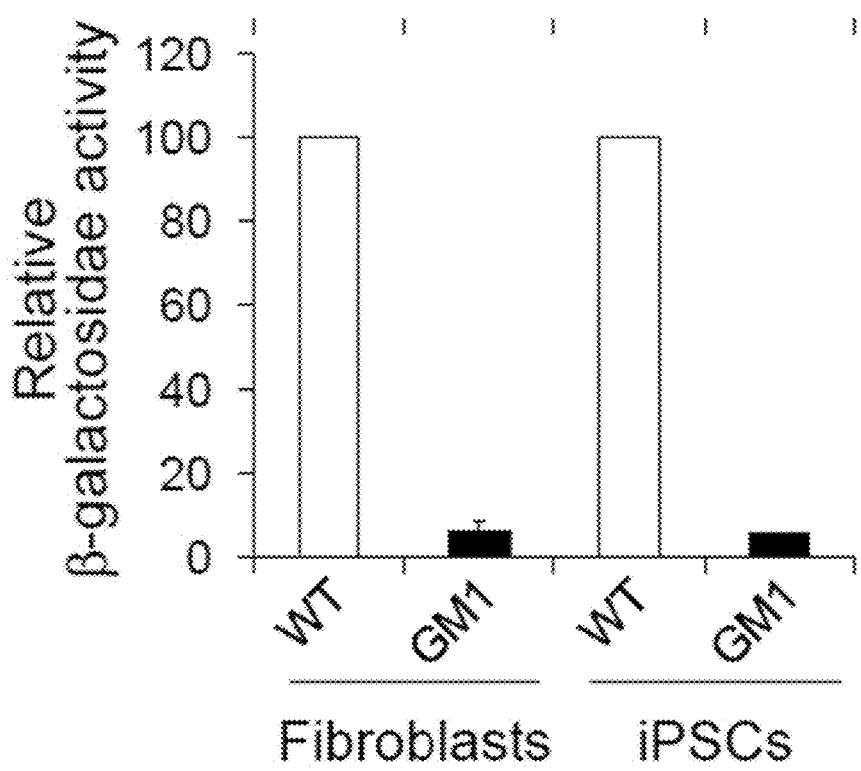

[Figure 14]
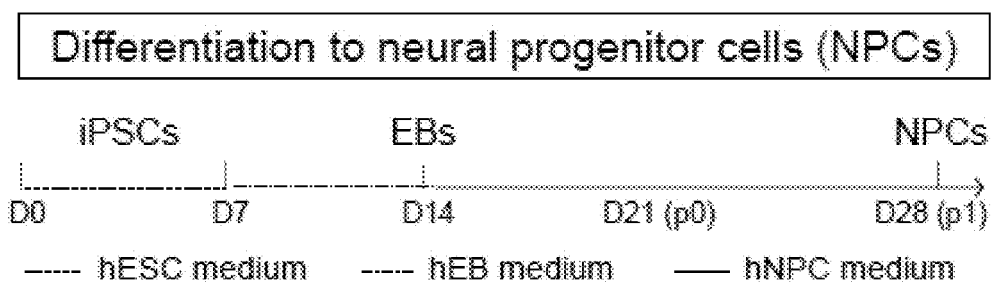

[Figure 15]
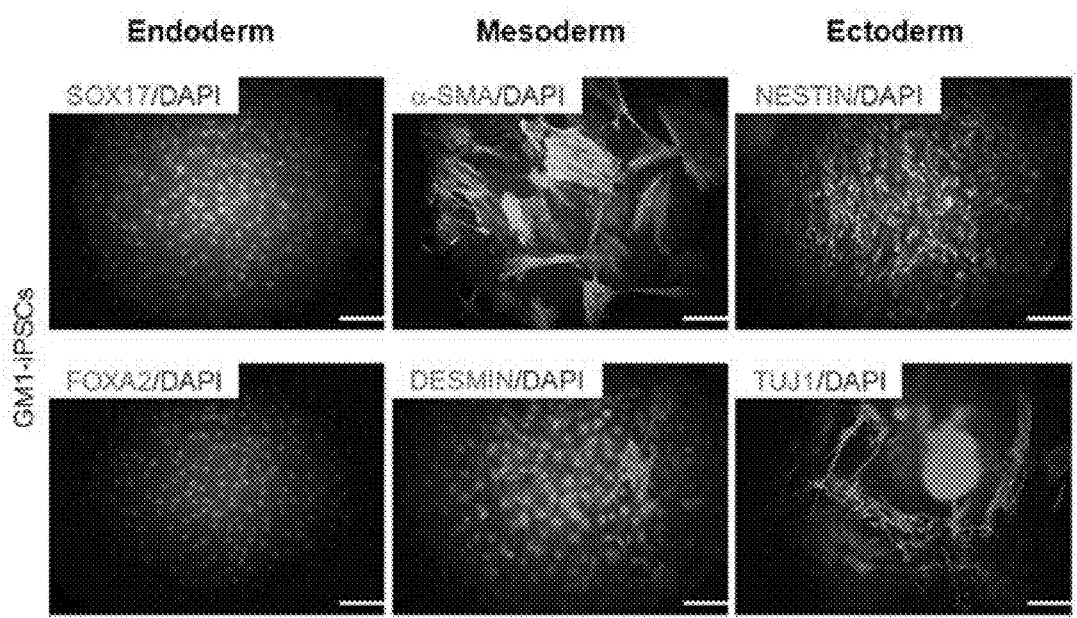

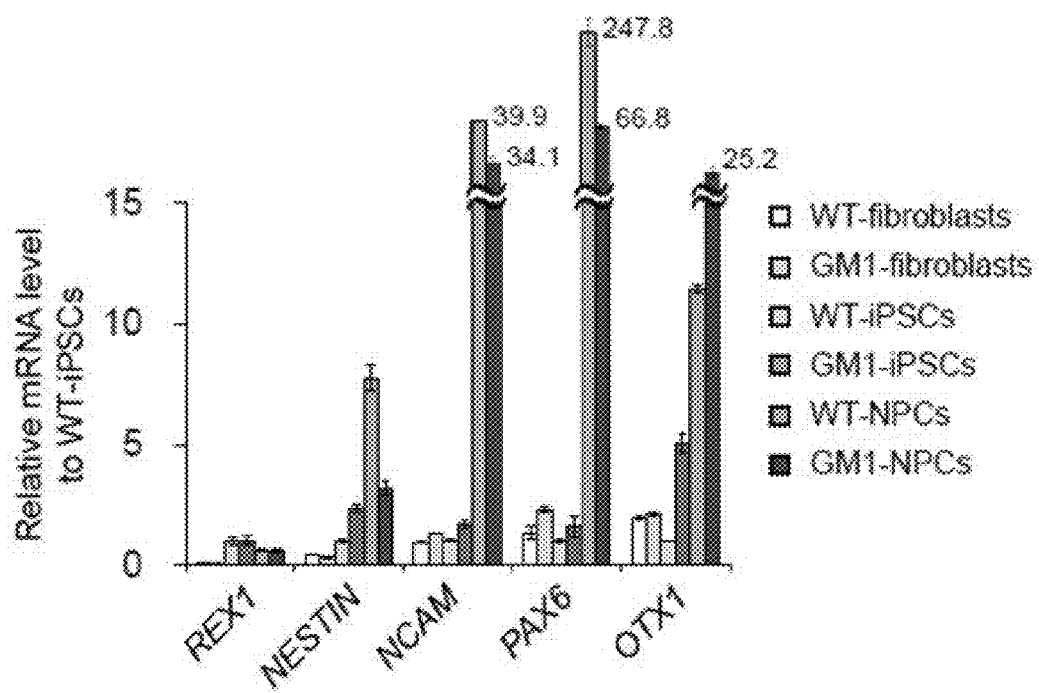
[Figure 16]

[Figure 17]
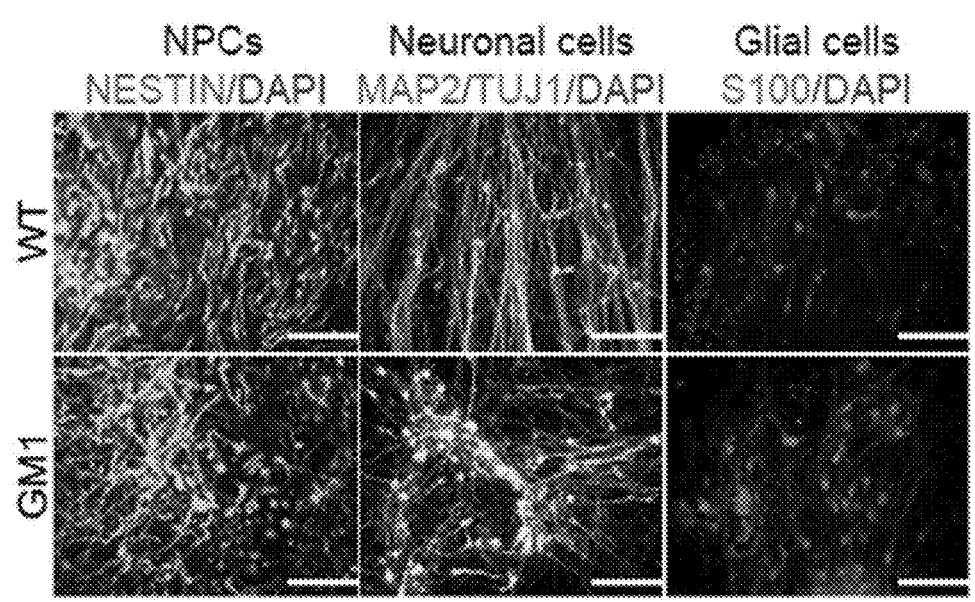

[Figure 18]
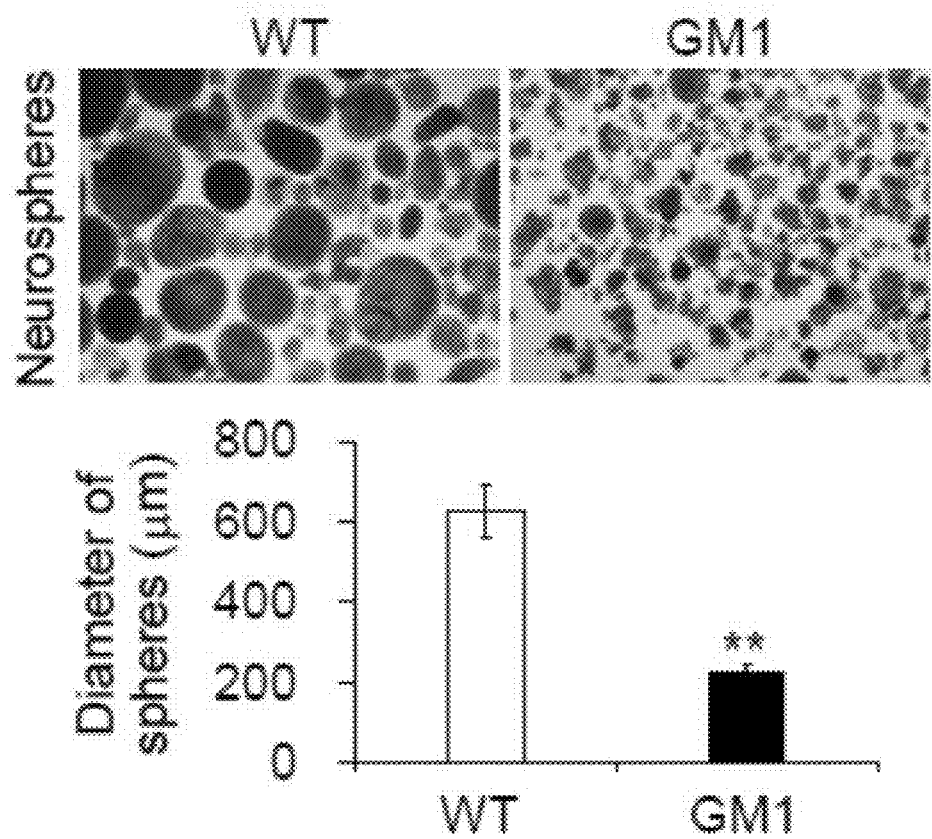

[Figure 19]
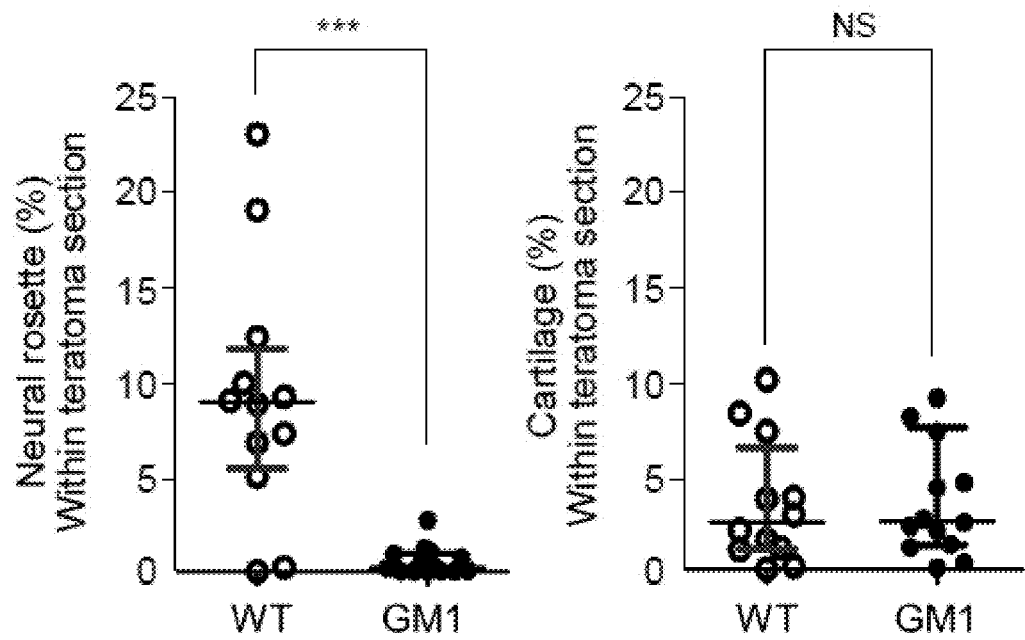

[Figure 20]

GM1 patient cells

Fibroblasts → iPSCs → NPCs

*GLB1* mutation
β-galactosidase deficiency
GM1 ganglioside accumulation
Lysosome increase

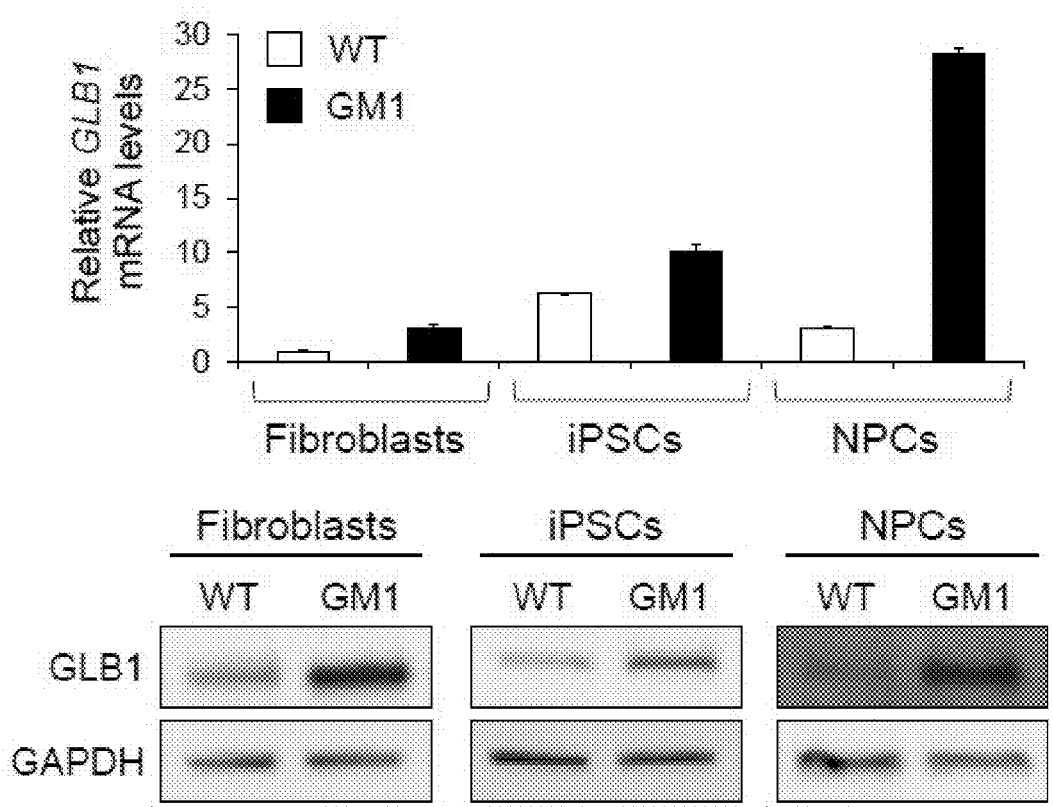
[Figure 21]

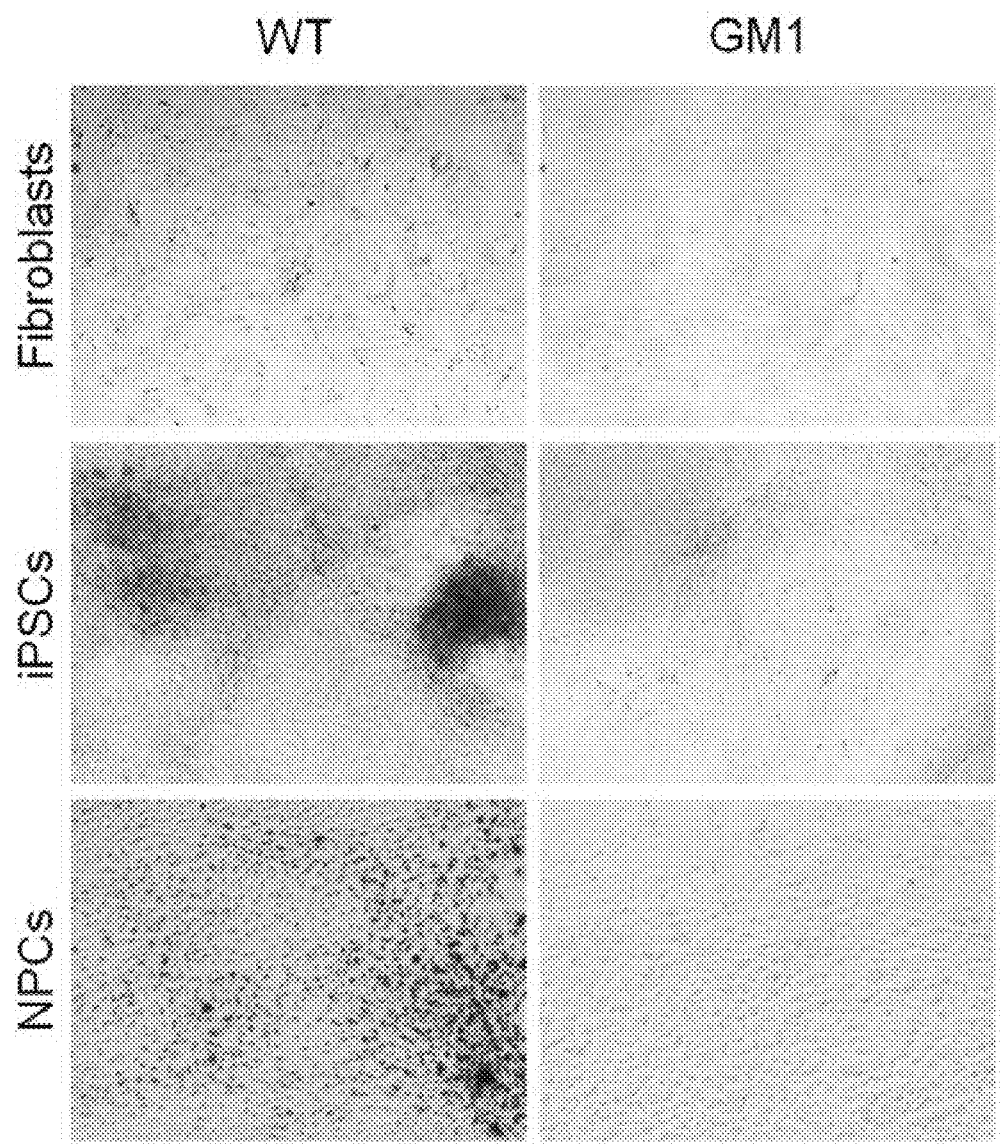
[Figure 22]

[Figure 23]
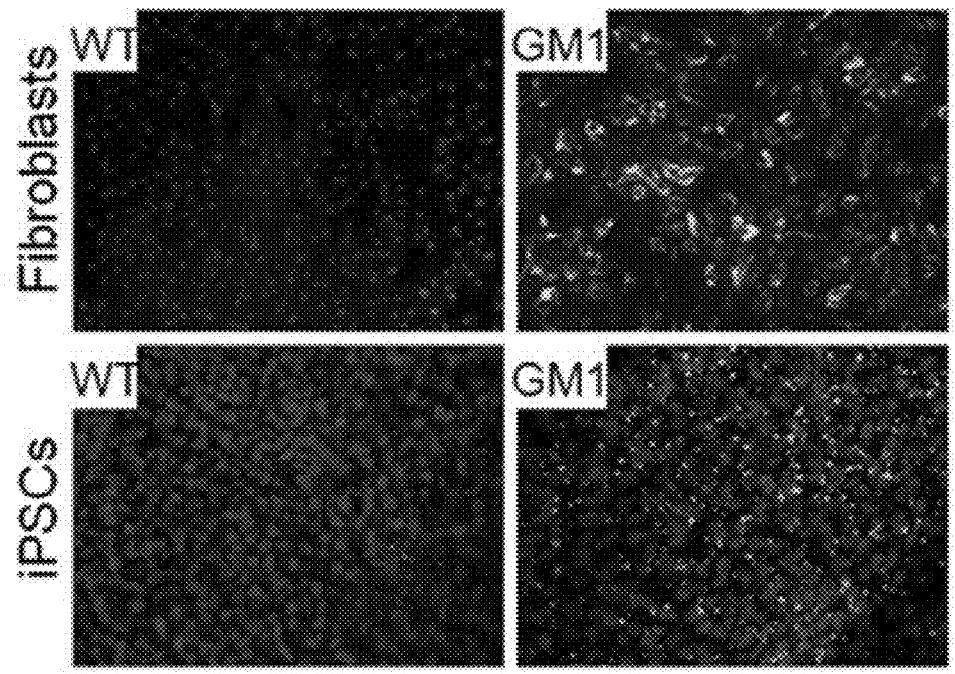
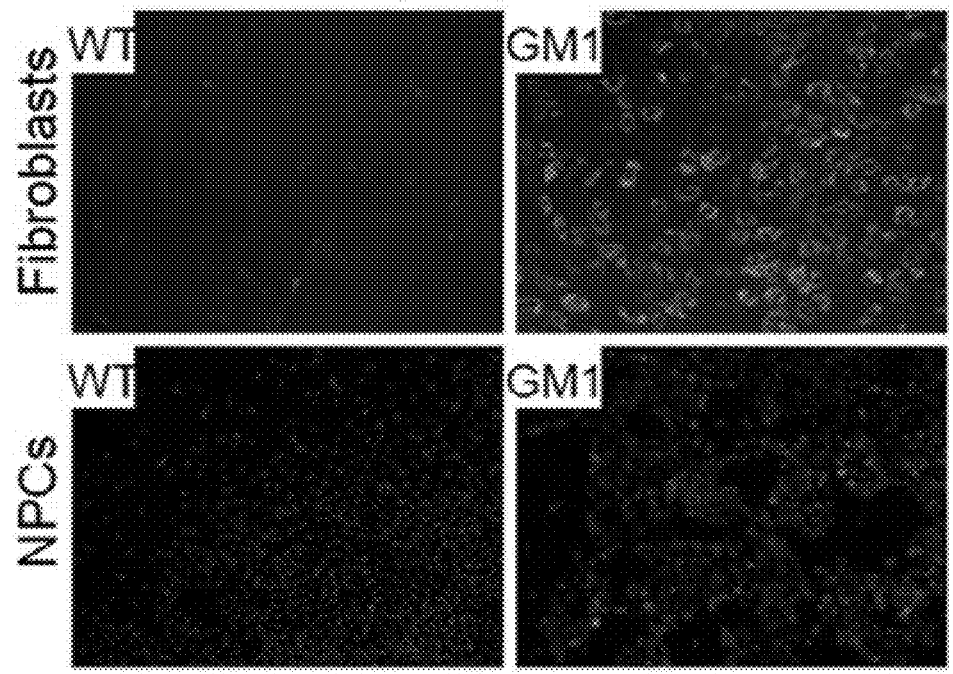

[Figure 24]
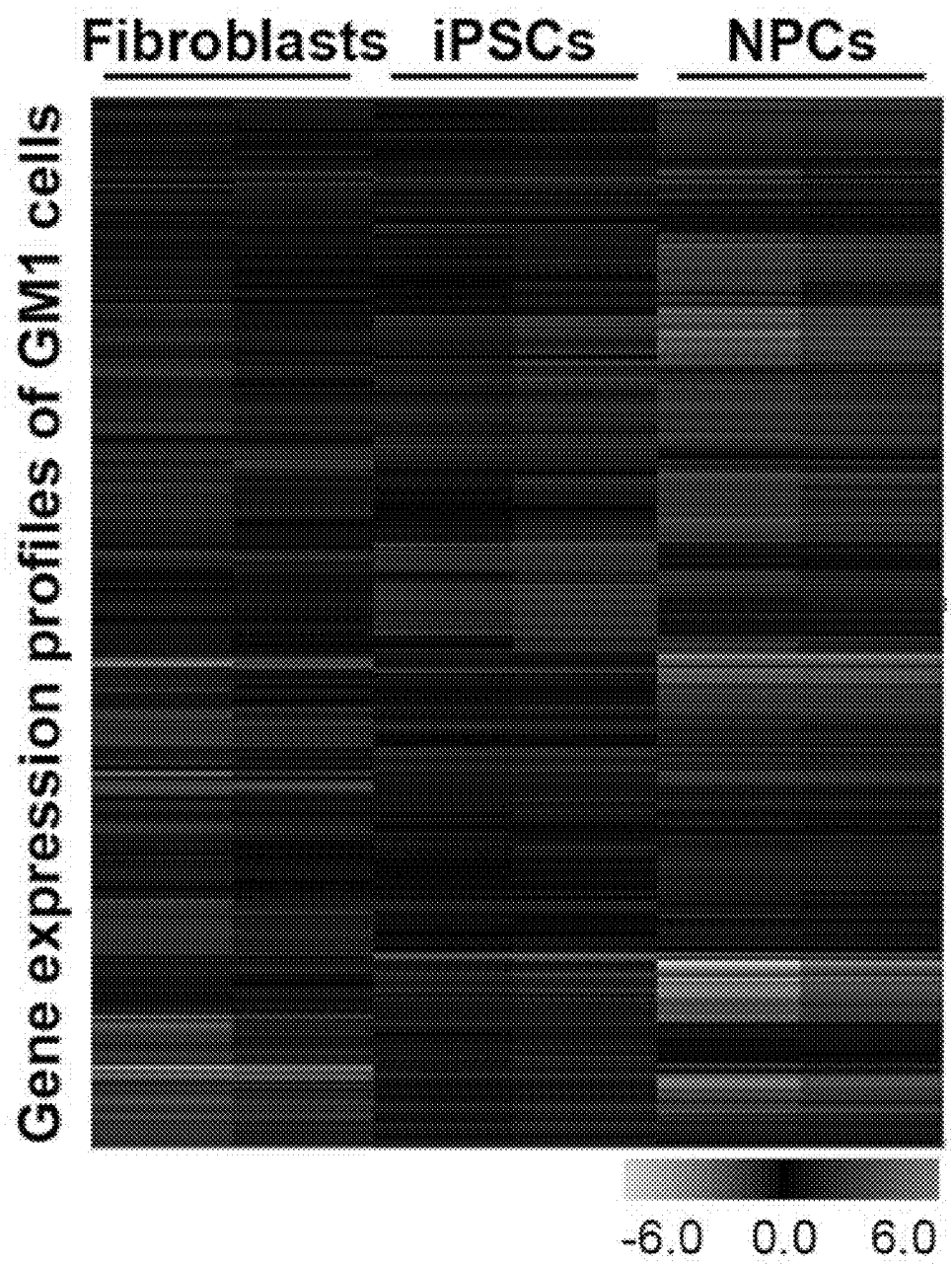

[Figure 25]
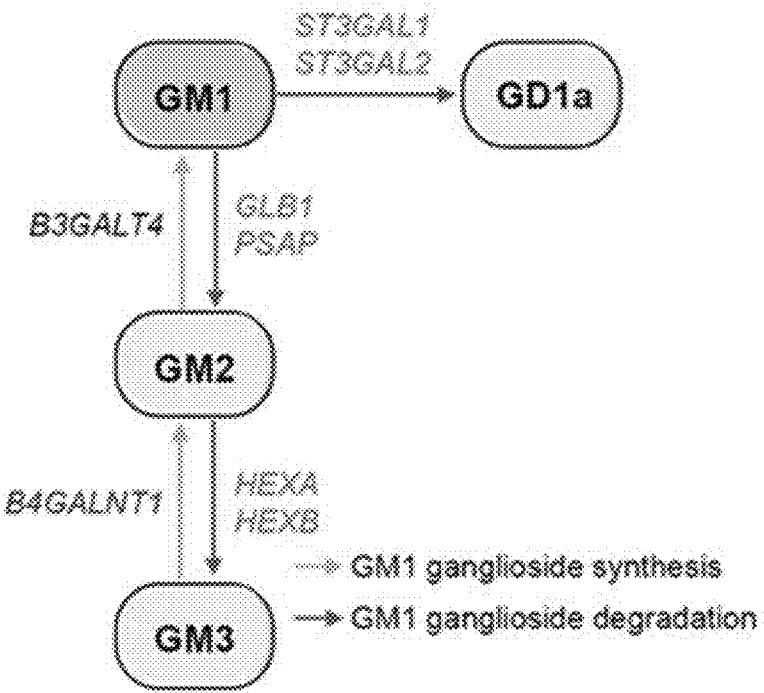
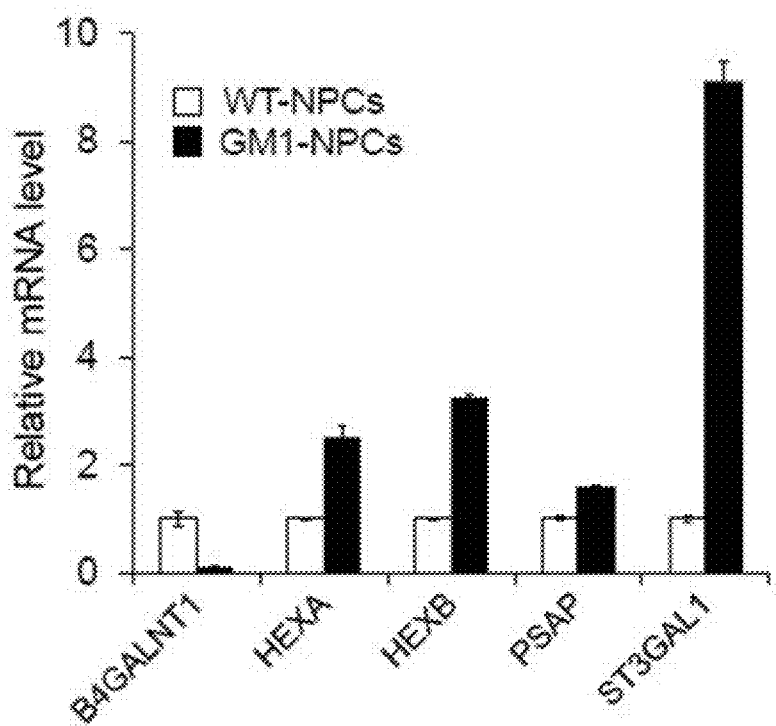

[Figure 28]
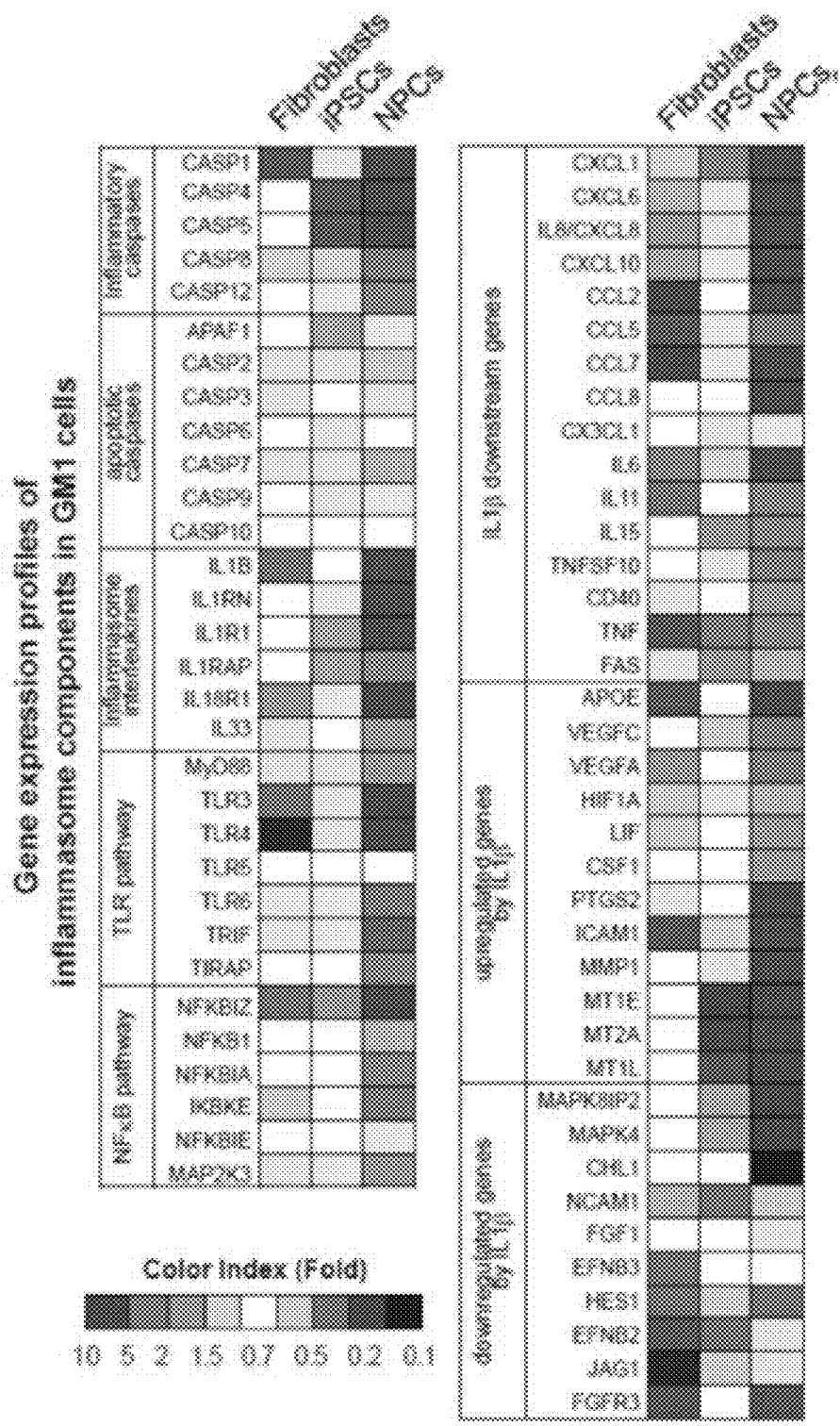

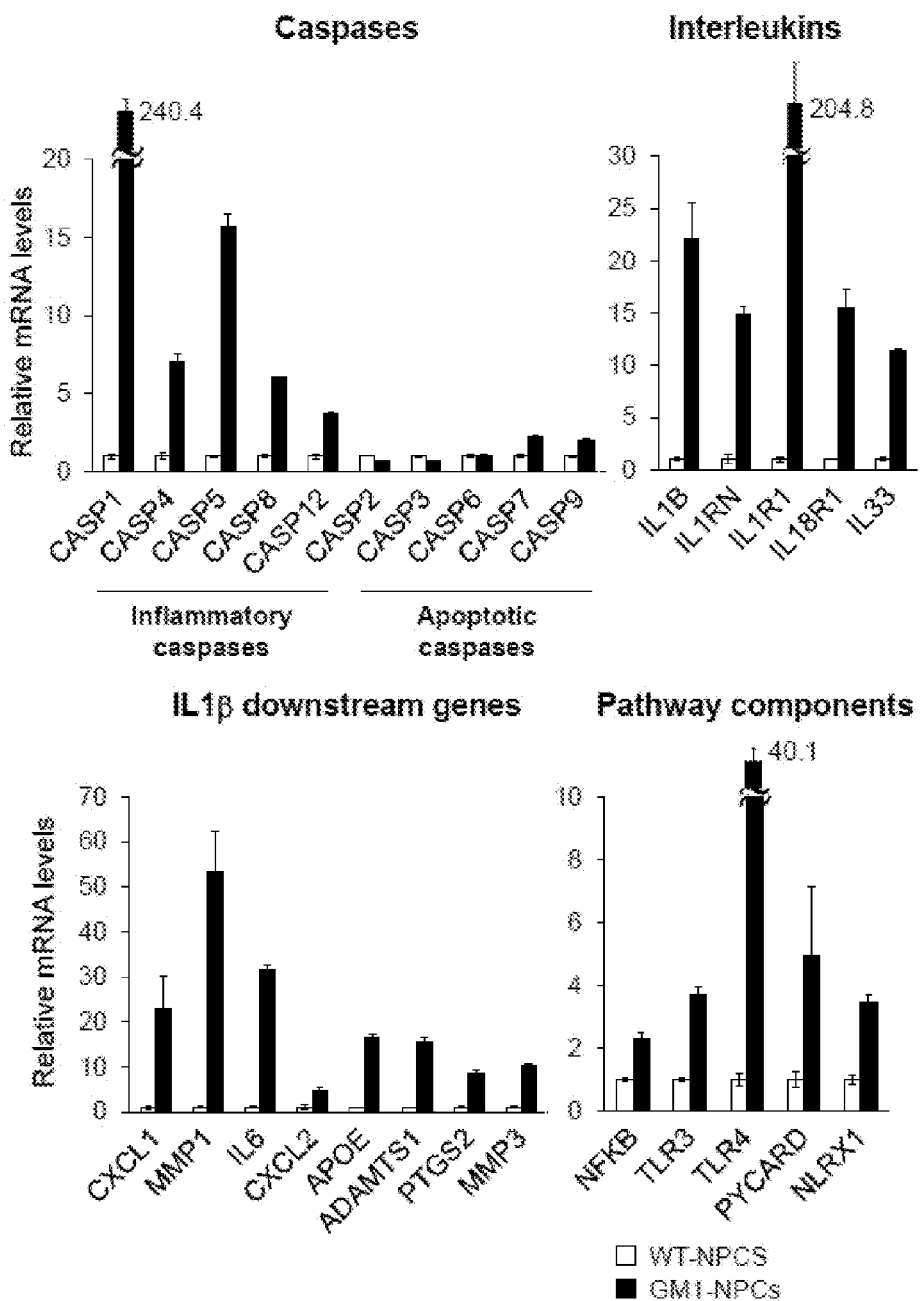
[Figure 29]

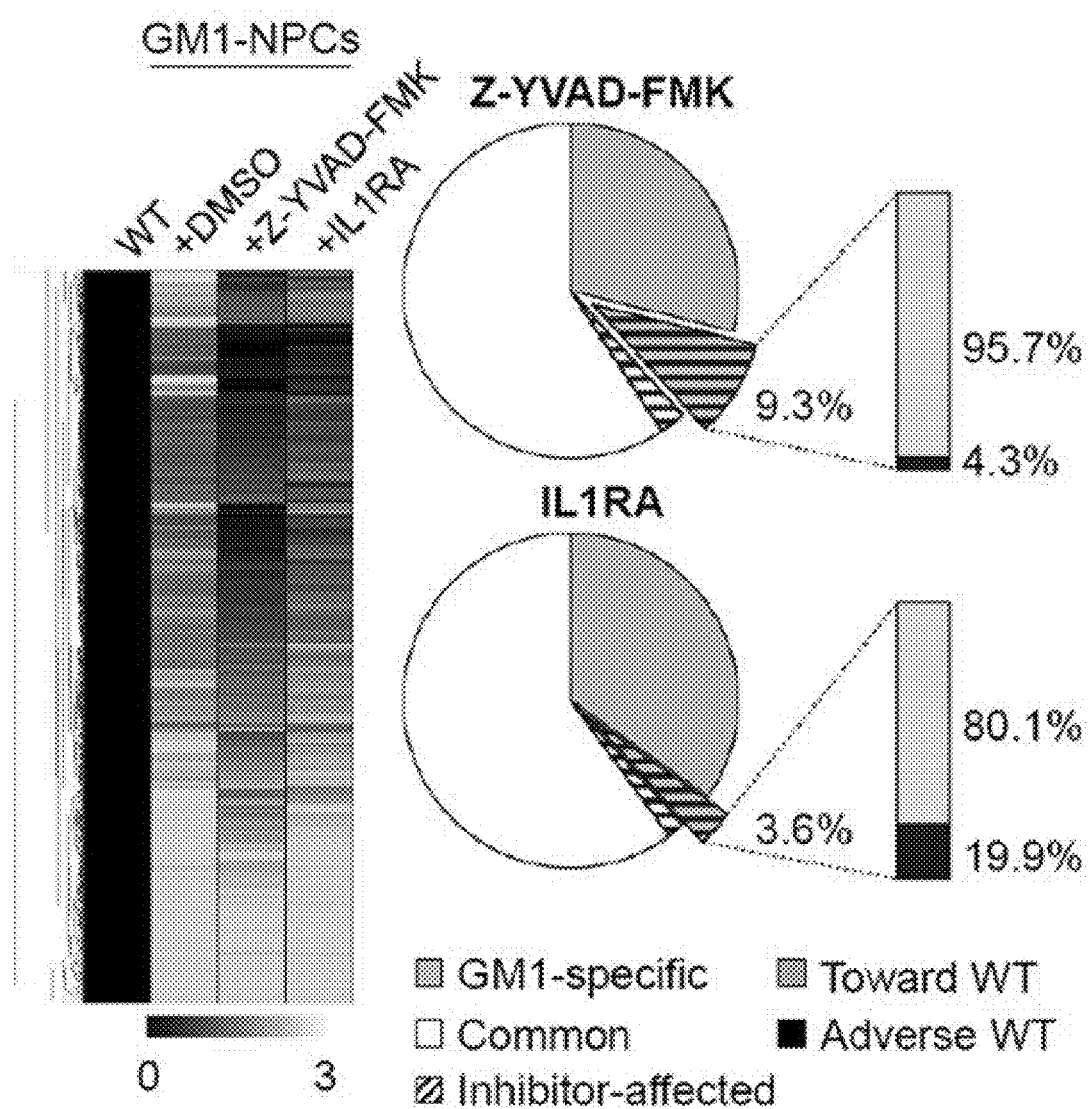
[Figure 31]

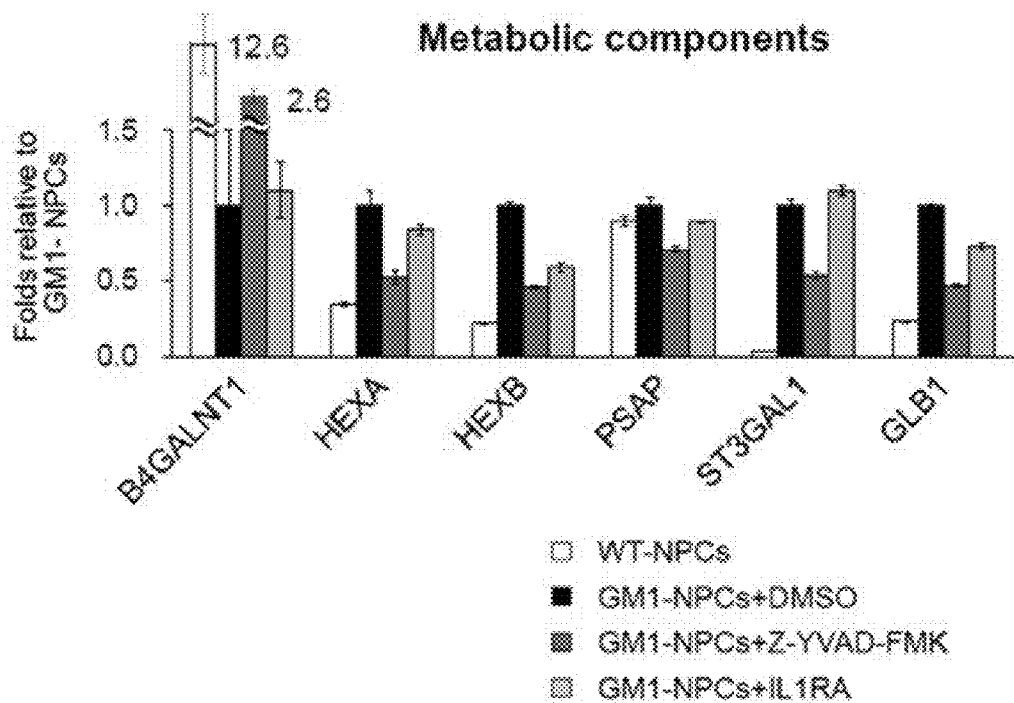
[Figure 32]

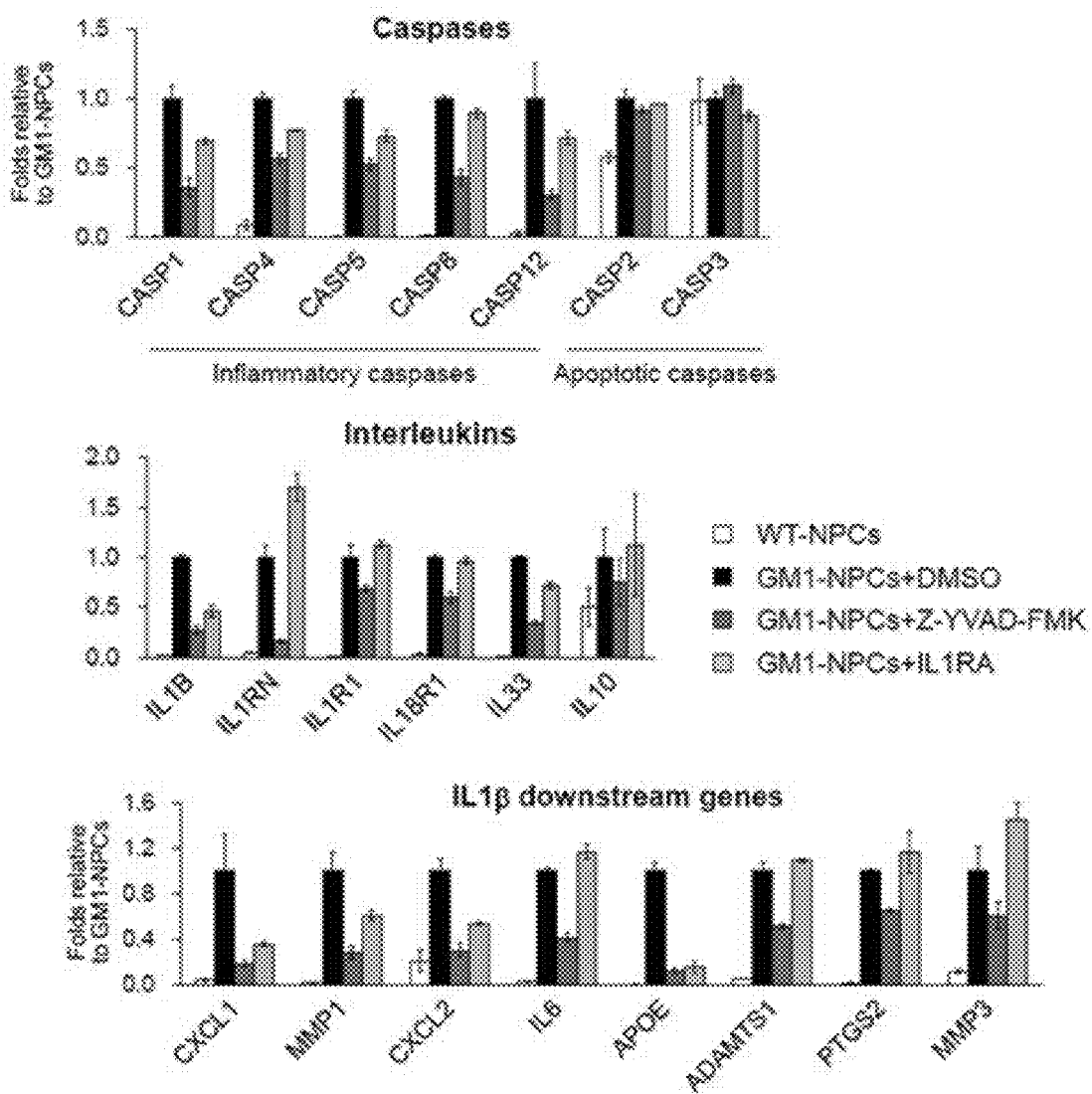
[Figure 33]

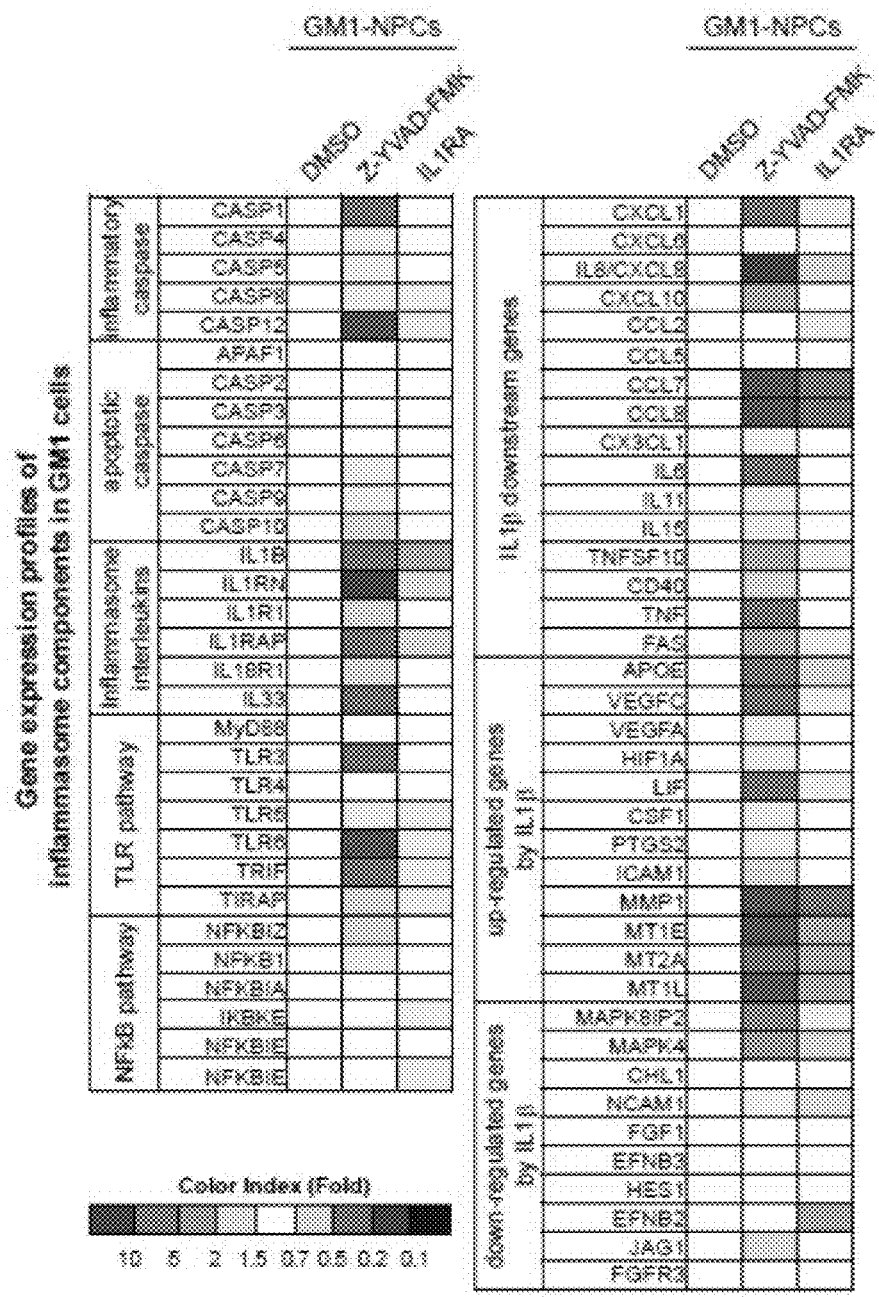
[Figure 34]

METHOD FOR TREATMENT OF GM1 GANGLIOSIDOSIS

CROSS REFERENCE TO RELATED APPLICATION

This is a continuation of International Application No. PCT/KR2014/011207, filed Nov. 20, 2014, which in turn claims the benefit of Korean Patent Application No. 10-2014-0118659, filed Sep. 5, 2014, and Korean Patent Application No. 10-2014-0162438, filed Nov. 20, 2014. The Korean applications are incorporated herein in their entirety.

BACKGROUND OF THE INVENTION

1. Field of the Invention

The present invention relates to a method for preparing a GM1 gangliosidosis human cell model by using the induced pluripotent stem cells (iPSCs) originated from GM1 gangliosidosis patient and by constructing the differentiated tissue-specific cells derived from the iPSCs, and a use of the said cell model for the screening of a GM1 gangliosidosis treating agent.

2. Description of the Related Art

GM1 gangliosidosis (GM1) is a very rare hereditary disease caused by deficiency of lysosomal β-galactosidase (β-gal), which is thus classified into lysosomal storage disease (LSD). β-gal is an enzyme encoded by GLB1 gene existing in lysosome, which plays a role in hydrolysis of various biomolecules (Brunetti-Pierri N and Scaglia F, *molecular genetics and metabolism* 94, 391-396, 2008). The most representative substrate of β-gal is GM1 ganglioside, the lysosomal sphingolipid. GM1 ganglioside is rich in the brain and plays an important role in the development and the general functions of nerve cells (Yu R K et. al, *Neurochemical research* 37, 1230-1244, 2012). The deficiency of β-gal activity leads to the accumulation of GM1 ganglioside in other cellular organs including endoplasmic reticulum (ER), and accordingly causes various symptoms including seizures, ataxia, and hepatosplenomegaly. The severity of such symptoms and the point of outbreak of disease are presumed to be related to the remaining β-gal activity. The most peculiar clinical symptom of GM1 is the progressive neurodegeneration in CNS. Thus, GM1 is basically understood as a neurological disorder and seems to share very similar characteristics with other neurodegenerative diseases (Vitner E B et. al, *The Journal of biological chemistry* 285, 20423-20427, 2010; Sandhoff K and Harzer K. *The Journal of neuroscience: the official journal of the Society for Neuroscience* 33, 10195-10208, 2013).

In the study on the developmental mechanism of GM1, the β-gal knock-out mouse model has been used. From which, various mechanisms responding to neuronal cell death such as unfolded protein response (UPR), mitochondrial dysfunction, increased autophagy, and activation of Trk signaling have been proposed (Tessitore A, et al. *molecular cell* 15, 753-766, 2004; Sano R, et al. *molecular cell* 36, 500-511, 2009; Takamura A, et al. *Biochemical and biophysical research communications* 367, 616-622, 2008; Takamura A, et al. *Journal of neurochemistry* 118, 399-406, 2011). The activation of inflammatory factor was once confirmed in the brain of β-gal$^{-/-}$ mouse. The progressive CNS inflammation is closely related to the clinical symptoms caused by such activation (Jeyakumar M, et al. *Brain: a journal of neurology* 126, 974-987, 2003). Chronic inflammation in CNS has been included in the criteria of neurodegenerative disease in a wide sense, and has been known to make abnormality in the brain structure and brain functions worse. Nevertheless, the molecular mechanism of the chronic neuroinflammation has not been fully studied.

The new role of inflammasome has recently confirmed in chronic inflammation related disease (Walsh J G et. al, *Nature reviews Neuroscience* 15, 84-97, 2014; Choi A M and Nakahira K, *Nature immunology* 12, 379-380, 2011; Franchi L et. al, *Nature immunology* 10, 241-247, 2009; Kufer T A and Sansonetti P J, *Nature immunology* 12, 121-128, 2011). According to the recent report, the said inflammasome is a protein complex composed of three kinds of proteins such as sensor protein, adaptor protein, and caspase-1. Various stimuli caused by infection, cell damage, and intracellular stress accelerate the formation of inflammasome and promote the activation of caspase-1. The activated caspase-1 induces the maturation of IL1β, the proinflammatory cytokine, and produces cytokine by secreting IL1β thereafter, resulting in the inducement of chronic inflammation. Therefore, inflammasome has been studied with immune cells including macrophages and microglias. Also, studies have been going on to prove any function of inflammasome in CNS neurons (Walsh J G et. al, *Nature reviews Neuroscience* 15, 84-97, 2014). More importantly, the activation of inflammasome has been explained as a molecular mechanism of the development of neurodegenerative disease including Alzheimer's disease and Parkinson's disease (Heneka M T, et al. *Nature* 493, 674-678, 2013). Amyloid-β well-known as the molecule that causes Alzheimer's disease induces the activation of inflammasome by destroying lysosome (Halle A, et al. *Nature immunology* 9, 857-865, 2008). Fibrillar α-synuclein playing an important role in causing Parkinson's disease can increase the production of ROS and make lysosome unstable to finally activate inflammasome (Codolo G, et al. *PloS one* 8, e55375, 2013).

The molecular mechanism related to human GM1 development has not been fully disclosed so far, so that the treatment of GM1 is still not possible. Even though GM1 mouse model has been constructed and this model can emulate many characteristics of human GM1, it can never be replaced with human GM1 and therefore study with GM1 mouse model will soon reach the limit. Therefore, the development of a human originated GM1 cell model that can reproduce the GM1 development mechanism will be very useful to understand the mechanism and cause of the disease and also to establish a more efficient treatment method.

Stem cells are the cells in the phase of pre-differentiation before being differentiated into each tissue forming cells, which can be obtained from the tissues of an embryo, a fetus, and an adult. Stem cells have self-proliferative activity that makes unlimited proliferation possible from undifferentiated status and have pluripotency, so that they can be differentiated into various tissue cells once a certain stimulus is given. That is, stem cells become to be differentiated by a certain differentiation stimulus (environment), and are self-renewal so as to produce the cells that are same as themselves by cell division, unlike the differentiated cells whose cell division has been finished. Stem cells also have proliferation/expansion capacity and plasticity, by which stem cells can be differentiated into different cells when the environment is changed or when a different stimulus is given.

Human pluripotent stem cells (hPSCs) including induced pluripotent stem cells (iPSCs) have excellent differentiation potency, so that they can be differentiated into almost every tissue cells forming human body. In particular, patient-originated iPSCs can produce tissue-specific differentiated cells showing immunologically and genetically same characteristics as the patient's, in the in vitro differentiation system. Thus, human pluripotent stem cells are well-known as the effective evaluator not only for the development of patient-customized cell therapy products which are free from worry on immune rejection response but also for understanding complicated disease mechanism in the early stage of organogenesis (Muotri, A. R. (2009) Epilepsy Behav 14 Suppl 1: 81-85; Marchetto, M. C., B. Winner, et al. (2010) Hum Mol Genet 19(R1): R71-76).

It was reported previously that when patient originated iPSCs obtained from patients with various genetic diseases were directly differentiated into disease-related cells, disease-specific phenotypes were observed (Park, I. H. et al. *Cell* 134, 877-886 (2008); Tiscornia, G. et al. *Nature medicine* 17, 1570-1576 (2011)). Such disease-specific iPSCs can be differentiated into those tissues that are directly involved in the cause of a disease or cell damage. So, the differentiated tissue-cell displaying disease specific characteristics can be used for the study on the mechanism to explain a cause of disease or for the development of a treating agent of the disease.

The present inventors tried to establish a human cell model for the study of GM1 gangliosidosis (GM1) based on patient-originated iPSCs. As a result, the inventors first constructed GM1 originated induced pluripotent stem cells (iPSCs) from fibroblasts of GM1 patient and then induced the differentiation of embryoid body (EB) and neural progenitor cells (NPCs) from the same. The GM1 patient derived iPSCs display both in vitro and in vivo pluripotency and at the same time have GM1 causing gene mutation detected in GM1 patient and accordingly show the reduced β-gal activity. The inventors also induced the differentiation of iPSCs originated from GM1 patient into neural progenitor cells. As a result, the expression of β-gal was increased but the activity thereof was reduced in the differentiated neural progenitor cells, suggesting that intracellular GM1 ganglioside and lysosome accumulation was increased. The gene expression pattern in the GM1 originated neural progenitor cells was compared with that of the normal cell. As a result, it was confirmed that inflammation related pathway, particularly inflammasome related metabolic pathway, was promoted. When the neural progenitor cells differentiated from GM1 patient derived iPSCs were treated with an inflammasome inhibitor, not only cell morphology and size but also gene expression pattern were recovered similarly to those of normal cells. The above results suggest that GM1 outbreak is related to inflammasome activation and therefore the inhibition of inflammasome is functioning to treat GM1. The present inventors examined disease-specific phenotype by using GM1 patient originated induced pluripotent stem cells (iPSCs) and iPSCs derived neural progenitor cells. As a result, it was suggested that inflammasome can be a key molecular target of the study to develop a GM1 treating agent and an inflammasome inhibitor displays positive effect on GM1 treatment. In conclusion, the present inventors completed this invention by proposing a novel GM1 gangliosidosis human cell model that can be efficiently used for the study of cause of GM1 and for the development of a therapeutic agent for the disease.

SUMMARY OF THE INVENTION

It is an object of the present invention to provide an improved method for the further study on GM1 gangliosidosis and an improved method for the development of a therapeutic agent for GM1 gangliosidosis by using the human cell model that can emulate the disease characteristics of GM1 gangliosidosis (GM1) patient, developed by the present inventors, by using induced pluripotent stem cells (iPSCs).

To achieve the above object, the present invention provides a GM1 gangliosidosis iPSCs model characterized by one or more of the following i)~vii):
  i) c.601C>T mutation of GLB1 gene;
  ii) R201C mutation of β-galactosidase (β-gal) protein;
  iii) normal cell morphology of iPSCs;
  iv) expression of pluripotency markers such as OCT4, NANOG, TRA-1-81, SSEA3, SSEA4, and TRA-1-60;
  v) up-regulation of GLB1 gene and β-gal protein;
  vi) decrease of β-gal activity; and
  vii) accumulation of GM1 ganglioside and lysosome.

The present invention also provides a method for constructing the GM1 ganglioside iPSCs model in vitro comprising the following steps:
  i) inducing induced pluripotent stem cells (iPSCs) in vitro from the fibroblasts separated from GM1 gangliosidosis (GM1) patient; and
  ii) collecting the iPSCs induced in step i).

The present invention further provides a GM1 gangliosidosis neural progenitor cell model characterized by one or more of the following i)~viii):
  i) expression of neural marker genes including NESTIN, NCAM, PAX6, and OTX2;
  ii) expression of neural marker proteins including MAP2, TUJ1, and S100;
  iii) cleaved cystic neurosphere;
  iv) decrease of neural rosette formation;
  v) up-regulation of GLB1 gene and β-gal protein;
  vi) decrease of β-gal activity;
  vii) accumulation of GM1 ganglioside and lysosome; and
  viii) up-regulation of inflammation related genes.

The present invention also provides a method for constructing the GM1 gangliosidosis neural progenitor cell model in vitro comprising the following steps:
  i) preparing induced-pluripotent stem cells in vitro from the fibroblasts separated from GM1 gangliosidosis patient;
  ii) inducing neural progenitor cells (NPCs) from the iPSCs prepared in step i); and
  iii) collecting the NPCs induced in step ii).

The present invention also provides a method for using the induced pluripotent stem cells (iPSCs), neural progenitor cells (NPCs), or neurosphere as the GM1 gangliosidosis model comprising the following steps:
  i) inducing the differentiation of GM1 gangliosidosis iPSCs into embryoid body (EB), neural progenitor cells (NPCs) or neurosphere; and
  ii) analyzing the differentiation markers of the embryoid body (EB), the characteristics of the neural progenitor cells (NPCs), or the morphological characteristics of the neurosphere induced in step i).

The present invention also provides a method for screening a treatment agent candidate for GM1 gangliosidosis comprising the following steps:
  i) treating the differentiated neural progenitor cells (NPCs) or neurosphere from the GM1 gangliosidosis iPSCs model with the sample compound or composition;
  ii) analyzing the characteristics of the neural progenitor cells (NPCs) or neurosphere of step 1); and
  iii) comparing the result obtained in step ii) with the non-treated control group.

The present invention also provides a pharmaceutical composition for the prevention and treatment of GM1 gangliosidosis comprising Z-YVAD-FMK (methyl(3S)-3-[(2S)-2-[(2S)-2-(2-{[(benzyloxy)carbonyl]amino}-3-(4-hydroxyphenyl)propanamido)-3-methylbutanamido]propanamido]-5-fluoro-4-oxopentanoate) as an active ingredient.

The present invention also provides a pharmaceutical composition for the prevention and treatment of GM1 gangliosidosis comprising interleukin-1 receptor antagonist protein as an active ingredient.

The present invention also provides a use of the GM1 gangliosidosis iPSCs model characterized by one or more of the following i)~vii):
 i) c.601C>T mutation of GLB1 gene;
 ii) R201C mutation of β-galactosidase (β-gal) protein;
 iii) normal cell morphology of iPSCs;
 iv) expression of pluripotency markers such as OCT4, NANOG, TRA-1-81, SSEA3, SSEA4, and TRA-1-60;
 v) up-regulation of GLB1 gene and β-gal protein;
 vi) decrease of β-gal activity; and
 vii) accumulation of GM1 ganglioside and lysosome.

The present invention also provides a use of the GM1 gangliosidosis neural progenitor cell model characterized by one or more of the following i)~viii):
 i) expression of neural marker genes including NESTIN, NCAM, PAX6, and OTX2;
 ii) expression of neural marker proteins including MAP2, TUJ1, and S100;
 iii) cleaved cystic neurosphere;
 iv) decrease of neural rosette formation;
 v) up-regulation of GLB1 gene and β-gal protein;
 vi) decrease of β-gal activity;
 vii) accumulation of GM1 ganglioside and lysosome; and
 viii) up-regulation of inflammation related genes.

The present invention also provides a method for the prevention and treatment of GM1 gangliosidosis containing the step of administering a pharmaceutically effective dose of Z-YVAD-FMK to a subject having GM1 gangliosidosis.

The present invention also provides a method for the prevention and treatment of GM1 gangliosidosis containing the step of administering a pharmaceutically effective dose of interleukin-1 receptor antagonist protein to a subject having GM1 gangliosidosis.

The present invention also provides a use of Z-YVAD-FMK as an active ingredient for the pharmaceutical composition of the present invention for the prevention and treatment of GM1 gangliosidosis.

The present invention also provides a use of interleukin-1 receptor antagonist protein as an active ingredient for the pharmaceutical composition of the present invention for the prevention and treatment of GM1 gangliosidosis.

The present invention also provides a GM1 gangliosidosis mutant cell model transformed with the β-gal mutant vector comprising E186A mutation in the amino acid sequence of β-gal protein.

The present invention also provides a method for constructing a GM1 gangliosidosis cell model in vitro comprising the following steps:
 i) constructing β-gal mutant vector comprising E186A mutation in the amino acid sequence of β-gal protein;
 ii) transforming the separated cells with the β-gal mutant expression vector constructed in step i); and
 iii) collecting the mutant cells transformed in step ii).

The present invention also provides a method for using the mutant cells transformed with the β-gal mutant vector comprising E186A mutation in the amino acid sequence of β-gal protein as the GM1 gangliosidosis cell model.

In addition, the present invention provides a use of the mutant cells transformed with the β-gal mutant vector comprising E186A mutation in the amino acid sequence of β-gal protein as the GM1 gangliosidosis cell model.

ADVANTAGEOUS EFFECT

The induced pluripotent stem cells (iPSCs) originated from the fibroblasts of GM1 gangliosidosis patient can be differentiated into neural progenitor cells (NPCs) and neurosphere cells that can emulate the disease-specific characteristics of GM1 patient, and the GM1 disease symptoms such as intracellular GM1 ganglioside/lysosome accumulation and also gene mutation can be confirmed in the cells. Therefore, the said cells have been successfully established as the GM1 model cells and thus the GM1 human cell model of the invention has been proposed as a useful model for the study on the GM1 development mechanism and for the development of a therapeutic agent for the disease.

In addition, the molecular symptoms of GM1 patient could be reproduced in the transformed cells having the E186A mutation which is newly identified as the GM1 gangliosidosis causing protein mutation. Therefore, the mutant cells containing the induced E186A mutation can be efficiently used as the GM1 gangliosidosis cell model.

BRIEF DESCRIPTION OF THE DRAWINGS

The application of the preferred embodiments of the present invention is best understood with reference to the accompanying drawings, wherein:

FIG. 1 is a schematic diagram illustrating the preparation process of the GM1 gangliosidosis (GM1)-derived iPSCs of the present invention and a use of the same.

FIG. 2a is a diagram illustrating the gene mutation of E186A, which is the protein mutation that causes GM1, in GM00918 cell line derived from GM1 patient; and FIG. 2b is a diagram illustrating the mutation of GM1 causing gene in GM02439 cell line derived from GM1 patient.

FIG. 3a is a diagram illustrating the accumulation of lysosome in fibroblasts originated from GM1 patient;

FIG. 3b is a diagram illustrating the accumulation of GM1 in fibroblasts originated from GM1 patient;

FIG. 3c is a diagram illustrating the activity of β-gal protein in fibroblasts originated from GM1 patient, confirmed by X-gal staining;

FIG. 3d is a diagram illustrating the decrease of R-gal activity in the cells transformed with the gene encoding the β-gal E186A mutant protein;

FIG. 3e is a diagram illustrating the activity of β-gal protein in the cells transformed with the gene encoding the β-gal E186A mutant protein, confirmed by X-gal staining; and FIG. 3f is a diagram illustrating the expression level of β-gal protein in the cells transformed with the gene encoding the β-gal E186A mutant protein.

FIG. 4a is a diagram illustrating the comparison of GLB1-related protein sequences between prokaryotes and eukaryotes;

FIG. 4b is a diagram illustrating the 3-dimensional structural analysis of the E186A mutant protein based on human β-gal protein; and FIG. 4c is a diagram illustrating the E186 residue site in the E186A mutant protein based on human β-gal protein.

FIG. 5 is a schematic diagram illustrating the construction process of induced pluripotent stem cells (iPSCs) from fibroblasts originated from GM1 patient.

FIG. 6 is a diagram illustrating the mutation of the GM1 causing gene in GM1-iPSCs and NPCs.

FIGS. 7A-7C present the characteristics of GM1-iPSCs:

FIG. 7a is a diagram illustrating the morphological characteristics of GM1-iPSCs;

FIG. 7b is a diagram illustrating the non-differentiation of GM1-iPSCs, confirmed by alkaline phosphatase staining (AP staining); and FIG. 7c is a diagram illustrating the expression of pluripotency marker protein in GM1-iPSCs.

FIG. 8 is a diagram illustrating the result of short tandem repeat (STR) assay of GM1-iPSCs.

FIG. 9 is a diagram illustrating the result of karyotype analysis of GM1-iPSCs.

FIG. 10 is a diagram illustrating the area size of teratoma differentiated from GM1-iPSCs in vivo.

FIG. 11 is a diagram illustrating the teratoma differentiated from GM1-iPSCs in vivo.

FIG. 12 is a diagram illustrating the activity of β-galactosidase (β-gal) in GM1-iPSCs, compared with that in fibroblasts.

FIG. 13a is a diagram illustrating the cell morphology of Epi-GM1-iPSCs, AP staining, and the expression of the pluripotency marker in the same;

FIG. 13b is a diagram illustrating the result of karyotype analysis of Epi-GM1-iPSCs; and FIG. 13c is a diagram illustrating the teratoma originated from Epi-GM1-iPSCs.

FIG. 14 is a schematic diagram illustrating the process of differentiation of GM1-NPCs from GM1-iPSCs.

FIG. 15 is a diagram illustrating the expressions of ectoderm, mesoderm, and endoderm markers of the embryoid body (EB) differentiated from GM1-iPSCs.

FIG. 16 is a diagram illustrating the mRNA expression of neural marker gene in GM1-NPCs differentiated from GM1-iPSCs.

FIG. 17 is a diagram illustrating the expression of neural marker protein in GM1-NPCs.

FIG. 18 is a diagram illustrating the morphology and the size of neurosphere originated from GM1-NPCs, wherein the red arrow indicates cystic neurosphere.

FIG. 19 is a diagram illustrating the differentiation of neural rosettes formed from GM1-iPSCs.

FIG. 20 is a schematic diagram illustrating the course of NPCs differentiation and the construction process of iPSCs from fibroblasts originated from GM1 patient and the symptoms shown in the cells of GM1 patient.

FIG. 21 is a diagram illustrating the expression level of GLB1 gene and protein in GM1-iPSCs and GM1-NPCs differentiated therefrom.

FIG. 22 is a diagram illustrating the activity of (3-gal in GM1-iPSCs and GM1-NPCs, confirmed by X-gal staining.

FIG. 23 is a diagram illustrating the accumulation of GM1-ganglioside and lysosome in GM1-iPSCs and GM1-NPCs.

FIG. 24 is a diagram illustrating the gene expression pattern in GM1-fibroblasts, GM1-iPSCs, and GM1-NPCs, confirmed by microarray.

FIG. 25 is a diagram illustrating the comparative expression level of GM1 metabolism related gene which is changed in GM1-fibroblasts, GM1-iPSCs, and GM1-NPCs.

FIG. 26a is a diagram illustrating the confirmation of UPR gene in GM1-fibroblasts, GM1-iPSCs, and GM1-NPCs; and FIG. 26b is a diagram illustrating the comparative mRNA expression level of UPR gene.

FIG. 27a is a diagram illustrating the course of expression increase which is double the expression in normal cells, confirmed by KEGG analysis; and FIG. 27b is a diagram illustrating the course of expression increase, confirmed by IPA analysis.

FIG. 28 is a diagram illustrating the result of microarray of the gene forming the inflammation response elements in GM1 patient derived cells.

FIG. 29 is a diagram illustrating the quantitative comparison of the mRNA expression of the gene forming the inflammation response elements in GM1 patient derived cells.

FIG. 30a is a diagram illustrating the morphology of the GM1-neurosphere differentiated by treating an inflammasome inhibitor;

FIG. 30b is a diagram illustrating the changes in cell diameter of the GM1-neurosphere differentiated by treating an inflammasome inhibitor; and FIG. 30c is a diagram illustrating the decrease of cystic neurosphere formation among the GM1-neurosphere differentiated by treating an inflammasome inhibitor.

FIG. 31 is a diagram illustrating the result of microarray of the GM1-neurosphere differentiated by treating an inflammasome inhibitor.

FIG. 32 is a diagram illustrating the expression of sphingolipid metabolism related enzyme in the GM1-neurosphere differentiated by treating an inflammasome inhibitor.

FIG. 33 is a diagram illustrating the gene expression pattern of inflammasome related pathway the GM1-neurosphere differentiated by treating an inflammasome inhibitor.

FIG. 34 is a diagram illustrating the result of microarray investigating the gene expression pattern of inflammasome related pathway in the GM1-neurosphere differentiated by treating an inflammasome inhibitor.

SEQUENCE LISTING

Figure 2A:
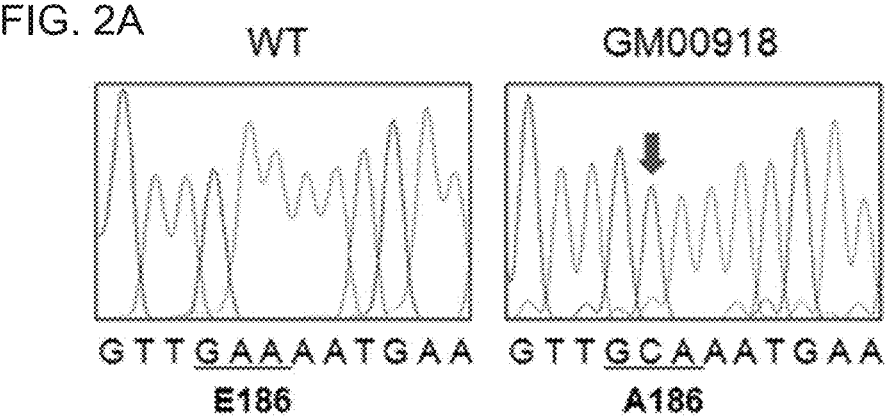
FIGS. 2A-2B present the GM1 causing gene mutation in GM1 patient originated fibroblasts.

The accompanying Sequence Listing is submitted as an ASCII text file in the form of the file named "Sequence.txt" (~4 KB), which was created on Sep. 29, 2015, and is incorporated by reference herein.

DESCRIPTION OF THE PREFERRED EMBODIMENTS

Hereinafter, the present invention is described in detail.

The present invention provides a GM1 gangliosidosis iPSCs model characterized by one or more of the following i)~vii):

i) c.601C>T mutation of GLB1 gene;
ii) R201C mutation of β-galactosidase (β-gal) protein;
iii) normal cell morphology of iPSCs;
iv) expression of pluripotency markers such as OCT4, NANOG, TRA-1-81, SSEA3, SSEA4, and TRA-1-60;
v) up-regulation of GLB1 gene and β-gal protein;
vi) decrease of β-gal activity; and
vii) accumulation of GM1 ganglioside and lysosome.

The present invention also provides a use of the GM1 gangliosidosis iPSCs model characterized by one or more of the following i)~vii):
i) c.601C>T mutation of GLB1 gene;
ii) R201C mutation of β-galactosidase (β-gal) protein;
iii) normal cell morphology of iPSCs;
iv) expression of pluripotency markers such as OCT4, NANOG, TRA-1-81, SSEA3, SSEA4, and TRA-1-60;
v) up-regulation of GLB1 gene and β-gal protein;
vi) decrease of β-gal activity; and
vii) accumulation of GM1 ganglioside and lysosome.

In a preferred embodiment of the present invention, the present inventors confirmed the GM1 mutant gene in fibroblasts originated from GM1 gangliosidosis patient (see FIG. 2), and constructed iPSCs (GM1-iPSCs) from the GM1 gangliosidosis patient fibroblasts (see FIGS. 5 and 6). Then, the inventors investigated the characteristics of the GM1-iPSCs. As a result, the GM1-iPSCs had pluripotency in vivo and in vitro and at the same time displayed the decrease of β-gal activity caused by the GM1 causing gene mutation observed in GM1 patient see FIGS. 7-13).

Since the GM1-originated iPSCs model of the present invention has pluripotency with displaying GM1 patient cell like characteristics, the iPSCs model can be efficiently used as a human cell model for the study of GM1 mechanism and for the development of a treating agent of the disease.

The present invention also provides a method for constructing the GM1 ganglioside iPSCs model in vitro comprising the following steps:
i) inducing induced pluripotent stem cells (iPSCs) in vitro from the fibroblasts separated from GM1 gangliosidosis (GM1) patient; and
ii) collecting the iPSCs induced in step i).

In the above method, the inducement in step i) is preferably performed by the ectopic expression of pluripotency marker. Particularly, the ectopic expression can be achieved by using retrovirus containing such reprogramming factors as OCT4, SOX2, C-MYC, and KLF4 or by transformation with the episome vector expressing the said reprogramming factors, or any other method to construct iPSCs well known to those in the art.

Since the GM1-originated iPSCs model of the present invention has pluripotency with displaying GM1 patient cell like characteristics, the iPSCs model can be efficiently used as a human cell model for the study of GM1 mechanism and for the development of a treating agent of the disease.

The present invention further provides a GM1 gangliosidosis neural progenitor cell model characterized by one or more of the following i)~viii):
i) expression of neural marker genes including NESTIN, NCAM, PAX6, and OTX2;
ii) expression of neural marker proteins including MAP2, TUJ1, and S100;
iii) cleaved cystic neurosphere;
iv) decrease of neural rosette formation;
v) up-regulation of GLB1 gene and β-gal protein;
vi) decrease of β-gal activity;
vii) accumulation of GM1 ganglioside and lysosome; and
viii) up-regulation of inflammation related genes.

The present invention also provides a use of the GM1 gangliosidosis neural progenitor cell model characterized by one or more of the following i)~viii):
i) expression of neural marker genes including NESTIN, NCAM, PAX6, and OTX2;
ii) expression of neural marker proteins including MAP2, TUJ1, and S100;
iii) cleaved cystic neurosphere;
iv) decrease of neural rosette formation;
v) up-regulation of GLB1 gene and β-gal protein;
vi) decrease of β-gal activity;
vii) accumulation of GM1 ganglioside and lysosome; and
viii) up-regulation of inflammation related genes.

The present invention also provides a method for using the induced pluripotent stem cells (iPSCs), neural progenitor cells (NPCs), or neurosphere as the GM1 gangliosidosis model comprising the following steps:
i) inducing the differentiation of GM1 gangliosidosis iPSCs into embryoid body (EB), neural progenitor cells (NPCs) or neurosphere; and
ii) analyzing the differentiation markers of the embryoid body (EB), the characteristics of the neural progenitor cells (NPCs), or the morphological characteristics of the neurosphere induced in step i).

In step ii), the embryoid body differentiation marker is preferably selected from the group consisting of the ectoderm markers NESTIN and TUJ1, the endoderm markers SOX17 and FOXA2, and the mesoderm markers α-smooth muscle actin (α-SMA) and DESMIN, but not always limited thereto.

The inflammasome related gene can be one or more genes selected from the group consisting of the inflammatory caspase related genes (Allan S M et. al, Nature reviews Immunology 5, 629-640, 2005; McIlwain D R et. al, Cold Spring Harbor perspectives in biology 5, a008656, 2013), the genes encoding proinflammatory cytokine including interleukine 1β (IL1β) and its downstream molecule (Walsh J G et. al, Nature reviews Neuroscience 15, 84-97, 2014; John G R et. al, Glia 49, 161-176, 2005; Liu L et. al, Journal of neuroinflammation 8, 175, 2011; Manso Y et. al, Journal of biological inorganic chemistry 16, 1103-1113, 2011), and any other genes related to the up-regulation of inflammasome, but not always limited thereto.

In another preferred embodiment of the present invention, the present inventors induced the differentiation of GM1 patient originated iPSCs (GM1-iPSCs) into embryoid body (EB) see FIG. 14). At this time, the expressions of all differentiation markers (ectoderm, endoderm, and mesoderm markers) were confirmed therein, suggesting that the GM1-iPSCs originated EB had differentiation potency (see FIG. 15). The differentiation of GM1-iPSCs into neuronal progenitor cells (GM1-NPCs) was also induced and as a result the mutation of the GM1 causing gene was still observed and the expression of the neural marker gene and protein was also confirmed (see FIGS. 6, 16, and 17). The GM1 originated neurosphere was smaller than the normal one and displayed cystic neurosphere like phenotype. The yield of neural rosette formation was also decreased (see FIGS. 18 and 19).

The present inventors also investigated whether or not the GM1 molecular phenotype remained unchanged in GM1-iPSCs and GM1-NPCs. As a result, the expression of GLB1 gene and protein was significantly increased (see FIGS. 20 and 21), while the activity of β-gal was significantly reduced and accordingly the accumulation of GM1 gangliosidosis and lysosome was increased (see FIGS. 22 and 23).

Figure 26A:
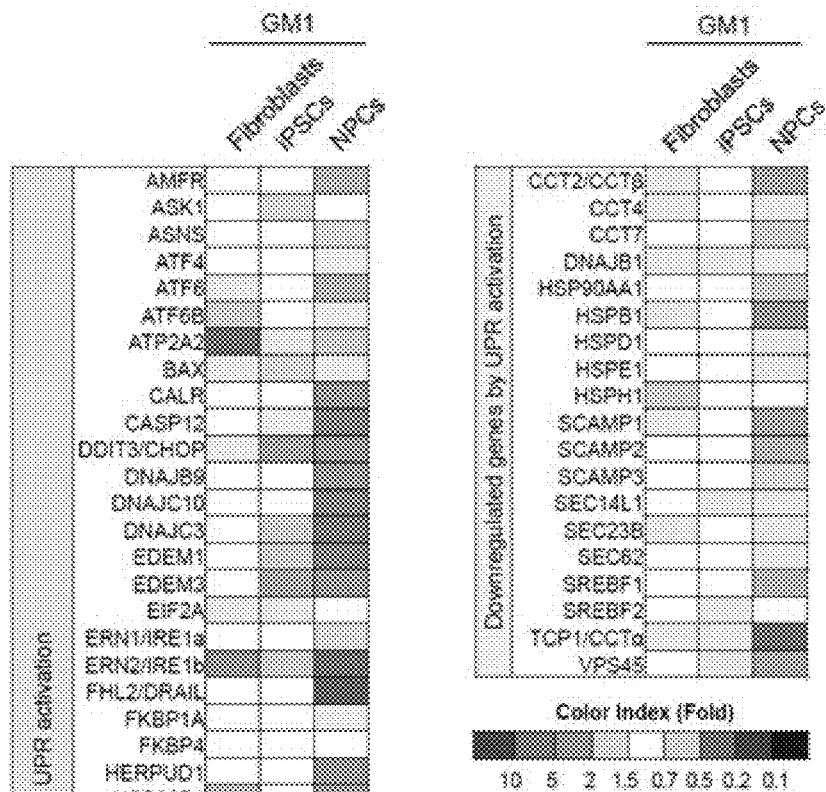
FIGS. 26A-26B present the gene expression pattern in GM1-fibroblasts, GM1-iPSCs, and GM1-NPCs, compared with the gene expression pattern previously reported to display unfolded protein response (UPR) in the GM1 mouse model.
Figure 26B:
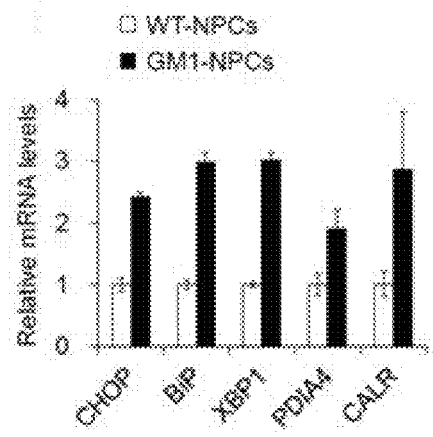

To investigate the development mechanism of GM1, the present inventors searched any gene that showed any change in its expression pattern in GM1-NPCs, compared with in normal cells. As a result, the gene expression which was significantly different from normal was confirmed in GM1 originated fibroblasts, iPSCs and NPCs, particularly in GM1-NPCs (FIGS. 24, 25, and 26). Particularly, the inflammation pathway related gene expression was increased, and inflammatory caspase, the inflammasome metabolic pathway gene, and those genes encoding IL1β and IL1β downstream molecules were also up-regulated (see FIGS. 27a~29).

Therefore, the GM1 patient originated iPSCs and the neural progenitor cells differentiated from the same of the present invention displayed GM1 patient cell like characteristics and also facilitates the investigation of the expression pattern of GM1 specific gene, so that the said iPSCs and neural progenitor cells of present invention can be efficiently used as a human cell model for the study of outbreak mechanism of GM1.

The present invention also provides a method for constructing the GM1 gangliosidosis neural progenitor cell model in vitro comprising the following steps:
 i) preparing induced-pluripotent stem cells in vitro from the fibroblasts separated from GM1 gangliosidosis patient;
 ii) inducing neural progenitor cells (NPCs) from the iPSCs prepared in step i);
 iii) collecting the NPCs induced in step ii).

The GM1 patient originated iPSCs and the neural progenitor cells differentiated from the same of the present invention displayed GM1 patient cell like characteristics and also facilitates the investigation of the expression pattern of GM1 specific gene, so that the said iPSCs and neural progenitor cells of present invention can be efficiently used as a human cell model for the study of outbreak mechanism of GM1.

The present invention also provides a method for screening a treatment agent candidate for GM1 gangliosidosis comprising the following steps:
 i) treating the differentiated neural progenitor cells (NPCs) or neurosphere from the iPSCs model of the invention with the sample compound or composition;
 ii) analyzing the characteristics of the neural progenitor cells (NPCs) or neurosphere of step 1); and
 iii) comparing the result obtained in step ii) with the non-treated control group.

In step ii), the characteristics of the neural progenitor cells (NPCs) or neurosphere are one or more preferably selected from the group consisting of the followings, but not always limited thereto:
 a) recovery from cystic neurosphere to normal neurosphere;
 b) increase in the size of neurosphere cells; and
 c) decrease of the expression of inflammation related gene.

The GM1 patient originated iPSCs and the neural progenitor cells differentiated from the same of the present invention could be recovered to normal cell like cell morphology and normal gene expression pattern when treated with an inflammasome inhibitor, so that the said iPSCs and neural progenitor cells can be efficiently used as a human cell model for the development of a treating agent of GM1.

In a preferred embodiment of the invention, the present inventors treated GM1-iPSCs with IL1β antagonist, the inflammasome inhibitor, and caspase-1 inhibitor in order to inhibit the increasing expression of inflammasome metabolism related genes which showed significant increase of the expression in GM1, and then induced the differentiation thereof into neurosphere cells. As a result, the differentiated neurosphere cells were recovered from the cystic cell shape to the normal cell shape, and accordingly the diameter of the cell was also increased (see FIG. 30). The present inventors also confirmed that when GM1-iPSCs was treated with an inflammasome inhibitor, the gene expression pattern was changed and precisely the expression of inflammasome factors, which was increased significantly in GM1-NPCs, was significantly decreased (see FIGS. 31~34).

The GM1 patient originated iPSCs and the neural progenitor cells differentiated from the same of the present invention can be recovered to normal cell like cell shape and normal gene expression pattern, when treated with an inflammasome inhibitor, suggesting that the said iPSCs and neural progenitor cells can be efficiently used as a human cell model for the development of a treatment agent of GM1.

The present invention also provides a GM1 gangliosidosis mutant cell model transformed with the β-gal mutant vector comprising E186A mutation in the amino acid sequence of β-gal protein.

The present invention also provides a method for constructing a GM1 gangliosidosis cell model in vitro comprising the following steps:
 i) constructing β-gal mutant vector comprising E186A mutation in the amino acid sequence of β-gal protein;
 ii) transforming the separated cells with the β-gal mutant expression vector constructed in step i); and
 iii) collecting the mutant cells transformed in step ii).

The present invention also provides a method for using the mutant cells transformed with the β-gal mutant vector comprising E186A mutation in the amino acid sequence of β-gal protein as the GM1 gangliosidosis cell model.

In addition, the present invention provides a use of the mutant cells transformed with the β-gal mutant vector comprising E186A mutation in the amino acid sequence of β-gal protein as the GM1 gangliosidosis cell model.

In a preferred embodiment of the present invention, the inventors investigated GLB1 gene mutation in genome of fibroblasts originated from GM1 patient. As a result, E186A, the novel GM1 causing gene mutation, was confirmed in GLB1 gene (see FIG. 2) and the cells displaying E186A mutation also showed the similar molecular symptoms to those observed in GM1 patient such as reduced β-gal activity and the intracellular accumulation of GM1 ganglioside (see FIGS. 3a~3c).

To investigate whether or not the E186A mutation was directly related to the decrease of β-gal activity in GM1 patient, the inventors measured the β-gal activity and expression in the cells transformed with the gene expression vector encoding the E186A mutant. As a result, the β-gal expression and activity were significantly reduced, compared with those in normal cells (see FIGS. 3d~3f).

In addition, in order to investigate the effect of E186A mutation on β-gal activity, structural analysis was performed. As a result, the mutation of GM1 causing protein containing E186A was confirmed to be induced in the genetically well preserved region in normal cells, suggesting that the mutation in the neighboring residues around β-gal active site can be a reason of the decrease of β-gal activity (see FIG. 4).

Therefore, since the molecular symptoms of GM1 patient can be reproduced in the transformed cells displaying the newly found E186A mutation, which is the mutation of the causing protein of GM1 gangliosidosis, the mutant cells containing E186A mutation can be effectively used as the GM1 gangliosidosis cell model.

The present invention also provides a pharmaceutical composition for the prevention and treatment of GM1 gangliosidosis comprising Z-YVAD-FMK (methyl(3S)-3-[(2S)-2-[(2S)-2-(2-{[(benzyloxy)carbonyl]amino}-3-(4-hydroxyphenyl)propanamido)-3-methylbutanamido]propanamido]-5-fluoro-4-oxopentanoate) as an active ingredient.

The present invention also provides a pharmaceutical composition for the prevention and treatment of GM1 gangliosidosis comprising interleukin-1 receptor antagonist protein as an active ingredient.

The present invention also provides a method for the prevention and treatment of GM1 gangliosidosis containing the step of administering a pharmaceutically effective dose of Z-YVAD-FMK to a subject having GM1 gangliosidosis.

The present invention also provides a method for the prevention and treatment of GM1 gangliosidosis containing the step of administering a pharmaceutically effective dose of interleukin-1 receptor antagonist protein to a subject having GM1 gangliosidosis.

The present invention also provides a use of Z-YVAD-FMK as an active ingredient for the pharmaceutical composition of the present invention for the prevention and treatment of GM1 gangliosidosis.

The present invention also provides a use of interleukin-1 receptor antagonist protein as an active ingredient for the pharmaceutical composition of the present invention for the prevention and treatment of GM1 gangliosidosis.

The said Z-YVAD-FMK is composed of the amino acid sequence represented by SEQ. ID. NO: 1 and presented as the structure shown in the below [Formula 1], but not always limited thereto.

The said Z-YVAD-FMK can be the caspase-1 inhibitor including caspase-1 inhibitor VI-calbiochem (product #: cat #218746; Merck Millipore), which can be any of those commercialized on the market.

[Formula 1]

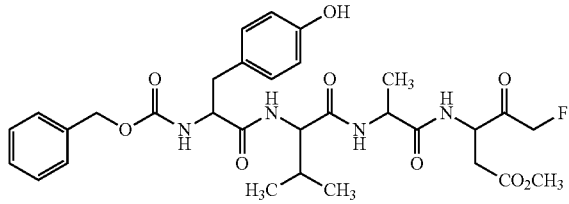

The said interleukin 1-receptor antagonist protein is composed of the amino acid sequence represented by SEQ. ID. NO: 2, but not always limited thereto.

The said interleukin 1-receptor antagonist protein is the interleukin 1-receptor antagonist protein such as IL1RA (product #: cat #280-RA-050 (rhIL-1ra); R&D systems), which can be any of those commercialized on the market.

The Z-YVAD-FMK or IL1RA of the present invention demonstrates the effect of recovering the GM1 patient-specific cell morphology and gene expression pattern to the normal ones in GM1-iPSCs and neural progenitor cells differentiated from the same, so that the said Z-YVAD-FMK or IL1RA can be efficiently used as an active ingredient of a pharmaceutical composition for the prevention and treatment of GM1 gangliosidosis.

The Z-YVAD-FMK or IL1RA of the present invention can be administered orally or parenterally and be used in general forms of pharmaceutical formulation. The parenteral administration includes intralectal, intravenous, intraperitoneal, intramuscular, intraarterial, transdermal, intranasal, intraocular, or subcutaneous injection, or inhalation.

That is, the Z-YVAD-FMK or IL1RA of the present invention can be prepared for parenteral administration by mixing with generally used diluents or excipients such as fillers, extenders, binders, wetting agents, disintegrating agents and surfactants. Formulations for parenteral administration are sterilized aqueous solutions, water-insoluble excipients, suspensions, emulsions, lyophilized preparations and suppositories. Water insoluble excipients and suspensions can contain polyethylene glycol, vegetable oil like olive oil, injectable ester like ethylolate, etc. Suppositories can contain witepsol, macrogol, tween 61, cacao butter, laurin butter, glycerogelatin, etc.

The Z-YVAD-FMK or IL1RA of the present invention can be mixed with many pharmaceutically acceptable carriers such as physiological saline or organic solvent, and can additionally include carbohydrates such as glucose, sucrose or dextran, antioxidants such as ascorbic acid or glutathione, chelating agents, low molecular proteins or other stabilizers to enhance stability or absorptiveness.

The effective dose of the Z-YVAD-FMK or IL1RA of the present invention is 0.01~100 mg/kg, preferably 0.1~10 mg/kg, and administration times are 1~3 per day.

The effective dose of the Z-YVAD-FMK or IL1RA of the present invention can be administered in the form of bolus by single dose having relatively short period of infusion or by multiple dose of fractionated treatment protocol for a long term. The decision of an effective dose depends on the administration pathway, treatment times, age and other conditions of a patient, etc. Therefore, any expert who has knowledge on this field can decide the effective dose of the Z-YVAD-FMK or IL1RA of the present invention.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Investigation of the Characteristics of GM1 Gangliosidosis (GM1) Cells <1-1> Confirmation of Novel Gene Mutation in GM1 Cells To investigate the GM1 causing gene mutation, the fibroblasts originated from GM1 gangliosidosis patient were cultured, followed by sequencing of GLB1 that is the causing gene of GM1 gangliosidosis.

Particularly, the fibroblast cell lines originated from GM1 gangliosidosis patients (GM00918, GM02439, GM03589, GM05335, GM05652, GM05653, GM10919, and GM12369) were first purchased from Coriell Institute for Medical Research, USA. GM00918, GM03589, GM05335, GM05652, GM05653, GM10919, and GM12369 cell lines were originated from those patients diagnosed in early childhood, and GM02439 cell line was originated from the patient diagnosed in adolescence (http://ccr.coriell.org). Each cell line was cultured in DMEM (Dulbecco's modified Eagle's medium) supplemented with 10% fetal bovine serum (FBS; Invitrogen, USA), 1% non-essential amino acids (NEAA; Invitrogen, USA), 1 mM L-glutamine (Invitrogen, USA), and 0.1 mM β-mercaptoethanol (Sigma, USA). Upon completion of the culture, RNA was extracted from the cultured cells by using RNAiso Plus (Takara, Japan) or RNeasy mini kit (Qiagen, USA) according to the manufacturer's protocol. Then, PCR was performed to synthesize GLB1 cDNA with the primers listed in Table 1 (SEQ. ID. NO: 3 and NO: 4) and Superscript III (Invitrogen, USA). The PCR product was electrophoresed on 1% agarose gel. The full-length band was cut out from the gel, followed by purification using QIAquick Gel Extraction Kit (Qiagen, USA). Whole sequence of GLB1 cDNA was analyzed with the purified oligomer using the primers listed in Table 1 (SEQ. ID. NO: 5~NO: 10). As for the control, the human skin originated wild-type fibroblast cell line CRL-2097 (American Type Culture Collection, ATCC) was used, from which GLB1 cDNA was synthesized by the same manner as described above, followed by sequencing thereof. This wild-type control was compared with the GM1 gangliosidosis cell line.

TABLE 1

|  | Forward | Reverse |
| --- | --- | --- |
| GLB1 cDNA synthesis | 5'-CCGCGGCCGCATGCCGGGGTTCCTGGTTCGCAT-3' (SEQ. ID. NO: 3) | 5'-GGCTCGAGTACATGGTCCAGCCATGAATC-3' (SEQ. ID. NO: 4) |
| GLB1 cDNA sequencing | 5'-CTATAGCCGGGACTCCTTCC-3' (SEQ. ID. NO: 5) 5'-CCCAGAGGGACACAGAATGT-3' (SEQ. ID. NO: 7) 5'-CGAGCATATGTTGCTGTGGATG-3' (SEQ. ID. NO: 9) | 5'-AGTTCCAGGGCACATACGTC-3' (SEQ. ID. NO: 6) 5'-CCTGCAGAAGCGCTTTCGCC-3' (SEQ. ID. NO: 8) 5'-GCCAGGCCGTGGGTCCTTAGTC-3' (SEQ. ID. NO: 10) |

As a result, as shown in Table 2, 6 kinds of missense mutation, 1 nonsense mutation, and 2 types of polymorphic mutation were confirmed in 8 of those GM1 patient originated cell lines (Table 2). All the GM1 patient originated cell lines, except GM03589, had homozygous mutation, and GM03589 cell line displayed two kinds of heterozygous mutation, which were confirmed to be responsible for the destruction of β-gal activity. p.P10L mutation was confirmed in 7 cell lines among those 8 cell lines, suggesting that this was the most common mutation. p.S352G mutation was confirmed in three of those cell lines, indicating this mutation is a cause of the decrease of β-gal activity. In addition, the previously reported GM1 specific gene mutations such as p.C127Y, p.R148S, p.W161C, p.R201C, and p.Q255H missense mutations and p.R351X nonsense mutation were confirmed in GM1 cell lines.

Figure 2B:
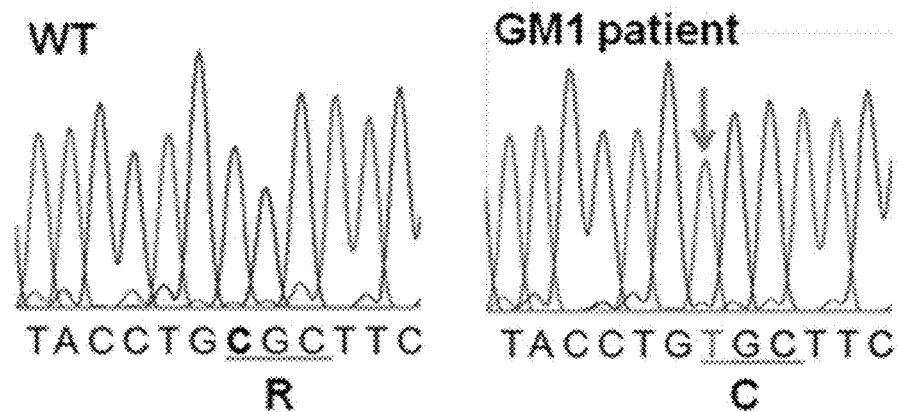

As shown in FIG. 2, pE186A mutation, the novel homozygous GM1 causing gene mutation, was confirmed in GM00918 cell line (FIG. 2a) and c.601C>T mutation in GLB1 gene was confirmed in GM02439 cell line, suggesting that the β-gal protein synthesized from the above gene showed R201C mutation (FIG. 2b).

<1-2> Investigation of the Characteristics of GM1 Patient Originated Fibroblasts To investigate the characteristics of GM1 patient cells, the characteristics of GM00918 displaying the novel E186A mutation newly identified as the GM1 causing gene mutation were investigated.

Particularly, GM00918 cell line was cultured in the same conditions as described in Example <1-1>. The culture medium was treated with LysoTracker Red DND-99 (1:20000; Invitrogen, USA), followed by reaction at 37° C. for 30 minutes. Then, the concentration of intracellular lysosome was measured. The cells were treated with 4% formaldehyde, followed by fixing at room temperature for 10 minutes. The cells were treated with PBS containing 0.1% triton X-100 for 15 minutes to give permeability to the cell membrane. Thereafter, the treated cells were washed with PBS containing 4% bovine serum albumin (BSA), and they were treated with the primary antibody 'anti-GM1 antibody (1:50; ab23943, Abcam, USA)' at 4° C. for overnight, followed by washing. The cells were treated with the secondary antibody conjugated with Alexa Fluor 488 or Alexa Fluor 594, and then left at room temperature for 2 hours. Then, the cells were observed under fluorescence

TABLE 2

GM1 causing gene mutation confirmed in GM1 patient originated cell line

| Cell line | Mutation type | Nucleotide variation Allele 1 | Nucleotide variation Allele 2 | Amino acid variation | Exon | Reference |
| --- | --- | --- | --- | --- | --- | --- |
| GM00918 | Polymorphic | C > T | C > T | P10L | 1 | (Callahan 1999) |
|  | Missense | A > C | A > C | E186A | 6 | this paper |
| GM02439 | Polymorphic | C > T | C > T | P10L | 1 | (Callahan 1999) |
|  | Missense | C > T | C > T | R201C | 6 | (Yoshida et al 1991) |
| GM03589 | Polymorphic | C > T | C > T | P10L | 1 | (Callahan 1999) |
|  | Missense | G > A | NC | C127Y (Het) | 3 | (Hofer et al 2010) |
|  | Missense | NC | T > G | W161G (Het) | 5 | (Caciotti et al 2011) |
| GM05335 | Missense | G > C | G > C | Q255H | 7 | (Iwasaki et al 2006) |
| GM05652 | Polymorphic | C > T | C > T | P10L | 1 | (Callahan 1999) |
|  | Nonsense | C > T | C > T | R351X | 10 | (Caciotti et al 2011) |
|  | Polymorphic | A > G | A > G | S532G | 15 | (Zhang et al 2000) |
| GM05653 | Polymorphic | C > T | C > T | P10L | 1 | (Callahan 1999) |
|  | Nonsense | C > T | C > T | R351X | 10 | (Caciotti et al 2011) |
|  | Polymorphic | A > G | A > G | S532G | 15 | (Zhang et al 2000) |
| GM10919 | Polymorphic | C > T | C > T | P10L | 1 | (Callahan 1999) |
|  | Missense | C > A | C > A | R148S | 4 | (Zhang et al 2000) |
|  | Polymorphic | A > G | A > G | S532G | 15 | (Zhang et al 2000) |
| GM12369 | Polymorphic | C > T | C > T | P10L | 1 | (Callahan 1999) |
|  | Missense | T > G | T > G | W161G | 5 | (Caciotti et al 2011) | microscope to investigate the accumulation of GM1 ganglioside. To compare the expression level, the cells were treated with 4'6-diamidino-2-phenylindole (DAPI) to stain nuclei.

To measure the β-gal activity, X-gal staining was performed. To do so, the buffer at a low pH (pH 4.5) was prepared with 50 mM citrate and 150 mM NaCl in order to replace PBS buffer above. X-gal staining was performed using β-gal staining kit (INtRon Biotechnology, Korea) according to the manufacturer's instruction. When blue color was shown, X-gal staining was terminated. The culture time was 4 hours~overnight according to the cell types. CRL2097 cell line was used as the control to compare the accumulation of lysosome. The fibroblasts originated from minimal brain dysfunction (MBD) patient were used as the control to compare the intracellular accumulation of GM1 ganglioside.

Figure 3A:
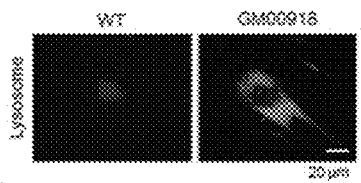
FIGS. 3A-3F present the characteristics of fibroblasts originated from GM1 patient.
Figure 3B:
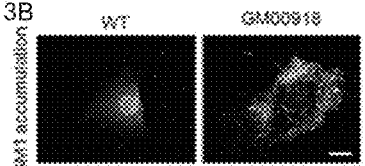
Figure 3C:
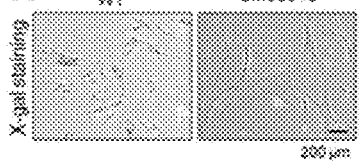

As a result, as shown in FIG. 3a and FIG. 3c, the lysosome accumulation was significantly increased in GM00918 cell line, compared with in the normal cell line CRL2097 (FIG. 3a). In the meantime, the huge accumulation of GM1 ganglioside was confirmed in GM00918 cell line, which was attributed to the decrease of β-gal activity, compared with that in the MBD patient originated cell line (FIGS. 3b and 3c).

<1-3> Investigation of the Cell Characteristics According to GM1 Mutation

To investigate whether or not the E186A mutation newly confirmed as the GM1 causing gene mutation could be a reason for the decrease β-gal activity, the inventors observed the GLB1 protein expression with or without E186A mutation in normal cells.

Particularly, GLB1 gene was amplified from CRL2097 cell line, the normal fibroblast cell line, which was inserted in pEGFP-N3 vector (BD bioscience Clonetech). FLAG tag was inserted in between 3'-end of GLB1 gene and 5'-end of GFP protein, resulting in the construction of a vector containing the wild-type GLB1 gene. Site-directed mutagenesis was induced in the site of E186A in GLB1 gene of the constructed vector, resulting in the construction of a vector containing the mutant GLB1 gene. The constructed vector containing the mutant GLB1 gene was introduced in 293T cell line for transfection in order to induce the expression of the mutant gene.

The cells transfected with the E186A GLB1 mutant gene vector were lysed in RIPA buffer, followed by centrifugation at 4° C. to eliminate the cell debris. 20~30 μg of the cell lysate proceeded to electrophoresis on 4~15% gel (Bio-Rad, USA) to separate the protein. The protein was transferred onto PVDF membrane (Bio-Rad, USA), followed by Western blotting using anti-GLB1 antibody (1:500; AF6464, R&D systems, USA). As for the control to correct the color development, GAPDH was stained by treating anti-GAPDH antibody. To confirm the β-gal activity, X-gal staining was performed by the same manner as described in Example <1-2>. As the normal control, the cells transfected with the vector containing the wild-type GLB1 gene were used. As the negative control, the cells transfected with the vector not containing GLB1 gene.

Figure 3D:
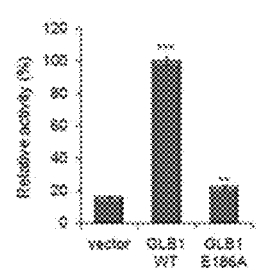
Figure 3E:
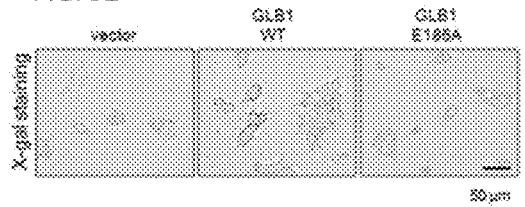
Figure 3F:
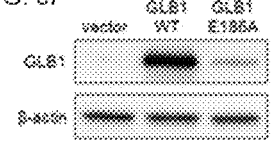

As a result, as shown in FIGS. 3d~3f, the β-gal activity in the negative control was 16% by that of the normal control, with confirming the β-gal activity expressed from the GLB1 of 293T genome. The β-gal activity in the cells transfected with the vector containing the mutant GLB1 gene was 22.9% by that of the normal control, which was similar level to that of the negative control (FIG. 3d). The β-gal activity reduction was confirmed by X-gal staining, compared with that of the normal control (FIG. 3e). The expression level of E186A β-gal mutant protein was reduced to 25% by the normal level, confirmed by Western blotting (FIG. 3f). Transformation was performed in many different manners with different conditions. As a result, it was confirmed that the E186A β-gal mutant protein level was not recovered to the level of the normal control with any of those trials, suggesting that this molecular characteristics was similar to that shown in GM1 patient cells.

<1-4> Structural Analysis of E186A Mutant Protein that is the GM1 Causing Protein To investigate the effect of E186A mutation in GLB1 protein on the decrease of activity, the structure of E186A mutant protein was analyzed by modeling.

Particularly, E186A mutation in GLB1 protein was arranged in the GLB1 sequence of human, mouse, *Drosophila*, *Arabidopsis*, *Trichoderma*, and *Arthrobacter* by using ClustalW2 and BoxShade server. For GLB1 modeling, the mutant model was made by using the human GLB1 crystal structure (PDB code: 3THC) as a template via PyMOL program.

Figure 4A:
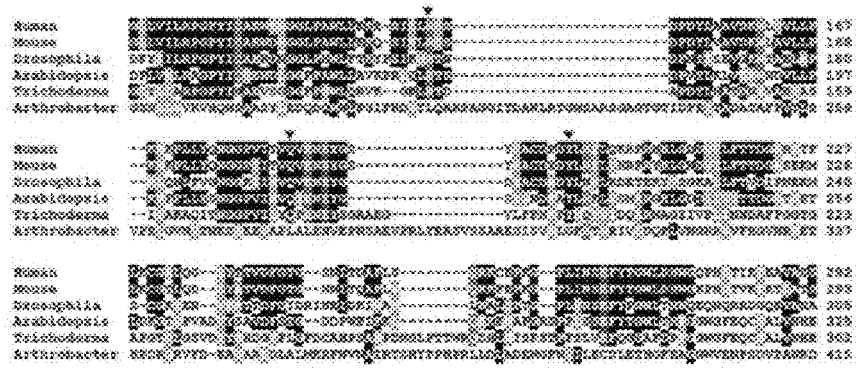
FIGS. 4A-4C present the structural analysis of the β-gal E186A mutant protein.
Figure 4B:
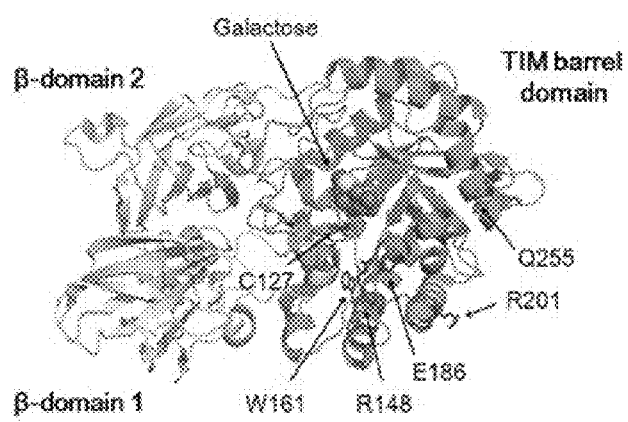
Figure 4C:
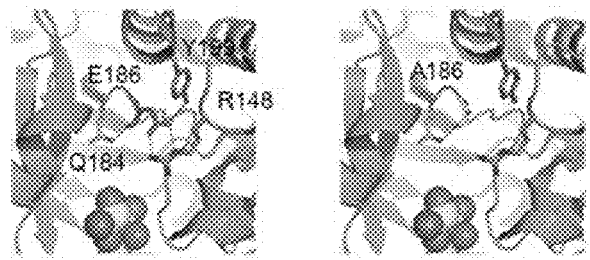

As a result, as shown in FIG. 4, the GLB1 related protein sequence of prokaryotes (*Arthrobacter*) was preserved in the GLB1 related protein sequence of eukaryotes such as fungi or human, but there was a difference observed in the catalystic residue preserved in eukaryotes and the homology containing total domain structure (FIG. 4a). The 6 kinds of missense mutation sites as shown in Table 2 are important for maintaining the protein functions. Particularly, R148 residue and E186 residue are well preserved, compared with the other four residues, and the sites of these two residues are close to the active E188 residue. Human β-gal protein crystal structure was three-dimensionally analyzed. As a result, it was confirmed that the residues on the sites of those 6 missense mutation were located in TIM barrel surrounding the active residues (FIG. 4b). Also, E186 residue was neighboring to R148, Q184, and Y199 residues, suggesting that E186 would be closely related to these residues (FIG. 4c). All the residues related to E186 residue were evolutionally well-preserved but these residues were mutated in GM1 patient gene. Therefore, the mutation of these residues was confirmed to have an effect on the functions of β-gal (FIG. 4a).

Example 2: Preparation of GM1 Originated Induced Pluripotent Stem Cells (iPSCs)

To execute the example of the invention, the inventors constructed iPSCs having pluripotency from GM1 patient fibroblasts (GM1-iPSCs) through the reprogramming culture using retrovirus expressing four reprogramming factors such as OCT4, SOX2, C-MYC, and KLF4 (Son M Y et. al, *Stem cells* 31, 2375-2387; 2013) (FIG. 5).

Particularly, GM02439, the GM1 patient originated fibroblast cell line confirmed with mutant gene in Example <1-1> was transfected with retrovirus encoding OCT4, SOX2, C-MYC, and KLF4, followed by culture in somatic cell medium for 5 days. 5 days later, the infected cells were transferred onto the matrigel-coated plate containing human embryonic stem cell culture medium (hESCs-CM), followed by additional culture for 2~3 weeks. Then, iPSC colonies were collected. GLB1 gene cDNA was synthesized from the obtained GM1-iPSCs by the same manner as described in Example <1-1>, followed by sequencing. For the control, the wild-type iPSCs (WT-iPSCs) were constructed from CRL-2097 by the same manner as described above.

As a result, as shown in FIG. 6, GM1-iPSCs were constructed from GM1 patient originated fibroblasts and they were confirmed to have c.601C>T mutation as equally to the mutation shown in GM1 originated fibroblasts (FIG. 6).

Example 3: Investigation of the Characteristics of GM1 Originated iPSCs

<3-1> Investigation of the Morphological Characteristics of GM1-iPSCs

To investigate the morphological characteristics of GM1-iPSCs, the colony type and karyotype of GM1-iPSCs were investigated, followed by short tandem repeat (STR) analysis.

Particularly, reprogramming of GM1-iPSCs was induced by the same manner as described in Example 2, and then the morphology of GM1-iPSCs colony formation was observed by phase-contrast microscopy. The present inventors asked GenDix Inc. (Korea) to perform karyotype analysis by chromosomal G-banding analysis. In addition, the inventors also asked HumanPass Inc. (Korea) to perform STR genotyping with GM1 originated fibroblast cell line (GM02439) and GM1-iPSCs, and the results were compared with the normal human embryonic stem cell line H9 hESCs.

As a result, as shown in FIGS. 7~9, GM1-iPSCs having pluripotency were successfully induced from GM1-fibroblast cell line (FIG. 8), and the constructed GM1-iPSCs demonstrated that their colony type and karyotype were similar to those of human embryonic stem cells (hESCs) (FIGS. 7a and 9).

<3-2> Alkaline Phosphatase (AP) Staining with GM1-iPSCs

To investigate the pluripotency of GM1-iPSCs originated from GM1 patient, alkaline phosphatase (pluripotent marker) staining (AP staining) was performed.

Particularly, fixative solution was prepared by mixing 1 ml of citrate solution, 2.6 ml of acetone, and 320 µl of 37% formaldehyde (Sigma Aldrich, USA) using alkaline phosphatase (AP) staining kit (Sigma Aldrich, USA). The prepared fixative solution was added to the GM1-iPSCs prepared in Example 2, which stood at room temperature for 15 minutes in the darkness. 100 µl of sodium nitrate solution was mixed with 100 µl of FRV-alkaline solution, and the mixture stood for 2 minutes. 4.5 ml of sterilized water and 100 µl of naphthol AS-Bl alkali solution were added thereto, and the mixture was stored as covered by aluminum foil to block the light. The fixed cells were washed with PBS once and loaded in the prepared AP staining mixture. The cells were washed with water or PBS twice for minutes each, and the AP stained cells were observed under phase contrast microscope.

As a result, as shown in FIG. 7b, it was confirmed that the GM1-iPSCs were positively stained with AP, the pluripotent marker (FIG. 7b).

<3-3> Confirmation of Pluripotency of GM1 Originated iPSCs

To confirm the pluripotency of the undifferentiated GM1-iPSCs originated from GM1 patient, the expression of the pluripotent marker protein in the GM1-iPSCs was observed.

Particularly, the GM1-iPSCs constructed in Example 2 were treated with 4% formaldehyde, followed by fixing at room temperature for 10 minutes. The cells were treated with PBS containing 0.1% triton X-100 for 15 minutes to give permeability to the cell membrane. Thereafter, the treated cells were washed with PBS containing 4% bovine serum albumin (BSA), and they were treated with the primary antibody anti-OCT4 antibody (1:100, sc-9081, Cruz Biotechnology, USA), anti-NANOG antibody (1:100, sc-33759, Cruz Biotechnology, USA), anti-TRA-1-81 antibody (1:100, MAB4381, Chemicon, USA), anti-SSEA3 antibody (1:100, MAB1435, R&D Systems, USA), anti-SSEA4 antibody, or anti-TRA-1-60 antibody (1:300, Millipore, USA) at 4° C. for overnight, followed by washing. The cells were treated with the secondary antibody (Invitrogen, USA) conjugated with Alexa Fluor 488 or Alexa Fluor 594, and then left at room temperature for 2 hours. Then, the cells were observed under fluorescence microscope to investigate the expressions of OCT4, NANOG, SOX2, SSEA4, Tra-1-80, and Tra-1-61 proteins. To compare the expression level, the cells were treated with 4'6-diamidino-2-phenylindole (DAPI) to stain nuclei.

As a result, as shown in FIG. 7c, the pluripotent markers OCT4, NANOG, TRA-1-81, SSEA3, SSEA4, and TRA-1-60 proteins were expressed in GM1-iPSCs at similar level to those of normal cells (FIG. 7c).

<3-4> In Vivo Confirmation of Pluripotency of GM1 Originated iPSCs

To investigate whether or not GM1 originated iPSCs had in vivo pluripotency, teratoma formation of GM1-iPSCs was induced in the immune deficient nude mouse model.

Particularly, $1 \times 10^6$ GM1-iPSCs constructed by the same manner as described in Example 2 were counted, which were transplanted in three SPF/VAF immune deficient nude mice (OrientBio, Korea) at 6 weeks of age. The animals were raised. 12 weeks later, the mice were sacrificed and teratoma was collected therefrom, to which 4% formaldehyde was added, followed by paraffin embedding. Then, H&E staining was performed by treating harris hematoxylin and eosin to confirm the formation of teratoma in endoderm, ectoderm, and mesoderm. To quantify the teratoma formation, each teratoma region was photographed and the size of each was calculated by using ImageJ software. As for the control, CRL2097 cells, the fibroblast originated iPSCs (WT-iPSCs), were injected in 5 mice by the same manner as described above to induce teratoma formation. The teratoma obtained from each mouse was sectioned into 2~5 pieces, which were used for the statistic analysis.

As a result, as shown in FIGS. 10 and 11, the teratoma originated from GM1-iPSCs was similar in the size to that of WT-iPSCs (FIG. 10). The teratoma formation was confirmed in ectoderm (nervous tissues and pigment cells), mesoderm (adipocytes, cartilage, and muscle), and endoderm (epithelium), but the differentiation into neurosphere was less observed than in WT-iPSCs (FIG. 11).

<3-5> Confirmation of GM1 Causing Protein Mutation in GM1-iPSCs

To investigate the characteristics of the mutant protein resulted from the mutation of GM1 causing gene in GM1-iPSCs, the activity of β-gal protein in GM1-iPSCs was investigated.

Particularly, the fibroblast cell line GM02439 and the GM1-iPSCs constructed by the same manner as described in Example 2 were suspended in the analysis buffer (pH 4.5) containing 10 mM citrate, 30 mM NaCl, and 1 mM $NgCl_2$. Then, the cells were lysed by 10 times repeated freeze/thaw, followed by centrifugation at 14,000 rpm at 4° C. for 5 minutes to eliminate the cell debris. 2 µg of the lysate was added to the analysis buffer containing 2 mM 4-methylumbelliferyl-β-D-galactopyranoside (MUG; Sigma-Aldrich, USA), followed by culture at 37° C. for 30 minutes. 30 minutes later, 0.1 M glycine-NaOH buffer (pH 10.5) at the half volume by the total volume of the reaction mixture was added to terminate the reaction. The concentration of 4-MU was calculated by measuring fluorescence intensity at 445 nm to confirm the β-gal activity. The β-gal activity of the control was also confirmed by the same manner as described above with the control CRL2097 and WT-iPSCs. Then, the comparative β-gal activity of GM1 fibroblasts and GM1-iPSCs was calculated and compared.

As a result, as shown in FIG. 12, it was confirmed that the β-gal activity of GM1-fibroblast cell line and GM1-iPSCs was approximately 7% by that of CRL2097 and WT-iPSCs (FIG. 12).

<3-6> Construction of GM1-iPSCs by Non-Viral Method.

To investigate whether or not another method to differentiate iPSCs could affect the characteristics of the cells, GM1-iPSCs were prepared by a different method from the one described in Example 2, which was the non-viral reprogramming method.

Particularly, 1×10⁶ GM02439 fibroblasts were counted and prepared, which were transfected with EBNA1/OriP-based pCET4 episomal vector expressing OCT4, SOX2, KLF4, NANOG, LIN28, L-MYC, and SV40LT by electroporation using Neon™ transfection system (Invitrogen, USA) according to the manufacturer's protocol. The conditions for electroporation were as follows: 1650 V pulse voltage, 10 ms pulse width, and 3 pulse. After the transfection by electroporation, the cells were inoculated on the 35 mm matrigel-coated well, followed by culture in iPSCs culture medium. The characteristics of the GM1 originated iPSCs induced by non-viral method (Epi-GM1-iPSCs) which were collected from the culture were investigated by observing colony morphology and karyotype, by performing AP staining, by measuring the expressions of the pluripotent markers OCT4, NANOG, TRA-1-81, SSEA3, SSEA4, and TRA-1-60, and by observing in vivo teratoma formation by the same manner as described in Examples <3-1>, <3-2>, <3-3>, and <3-4>.

Figure 13A:
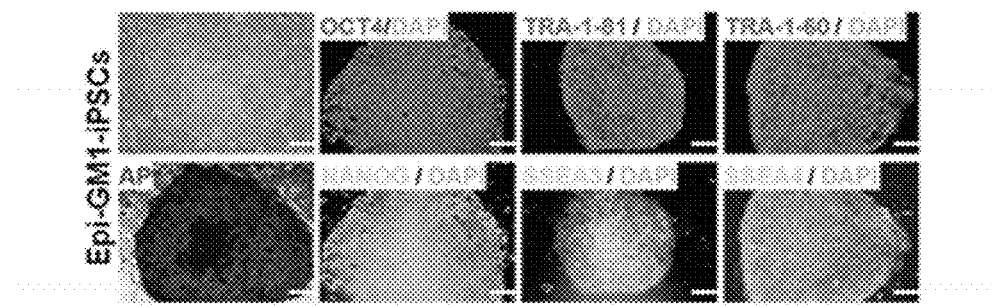
FIGS. 13A-13C are diagrams illustrating the characteristics of Epi-GM1-iPSCs constructed by the non-viral method.
Figure 13B:
Figure 13C:
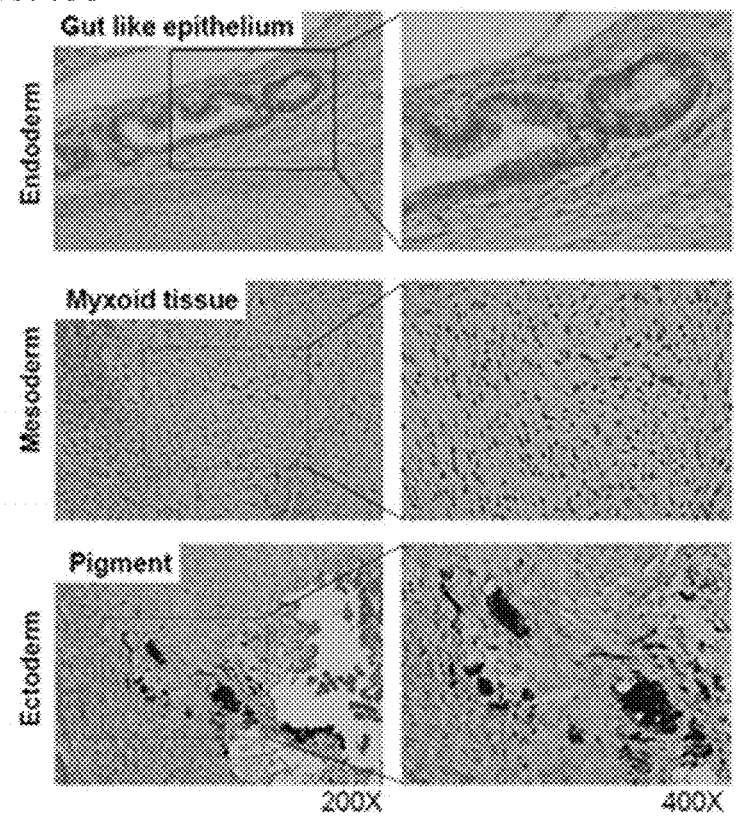

As a result, as shown in FIG. 13, the Epi-GM1-iPSCs prepared by transfecting the cells with pCET4 episomal vector displayed the characteristics similar to those of the GM1-iPSCs prepared by transfecting the cells with retrovirus. Therefore, it was confirmed that the characteristics of iPSCs did not changed according to the inducement method (FIG. 13).

Example 4: Differentiation of GM1 Originated Neural Progenitor Cells (NPCs)

<4-1> Inducement of the Differentiation of Embryoid Body (EB) and Neural Progenitor Cells (NPCs) from GM1-iPSCs To induce the differentiation of GM1 originated neuronal cells in vitro from GM1-iPSCs, the differentiation of embryoid body (EB) and neural progenitor cells (NPCs) was induced from GM1-iPSCs according to the schematic diagram shown in FIG. 14 (FIG. 14).

Precisely, the GM1-iPSCs colony induced by reprogramming for 7 days by the same manner as described in Example 2 was cultured in embryoid body differentiation medium (DMED/F12 containing 10% serum replacement (SR)) for 7 days to induce the differentiation of GM1-iPSCs originated embryoid body (GM1-EB). The differentiated GM1-EB was further cultured in NPCs medium (DMEM/F12 supplemented with 1×N2/B27 (Invitrogen, USA), 20 ng/ml bFGF, 20 ng/ml EGF (Invitrogen, USA), and 10 ng/ml leukemia inhibitory factor (Sigma-Aldrich, USA)) for 2 more weeks. Then, the differentiated GM1 originated neural progenitor cells (GM1-NPCs) were collected. During the period of the differentiation culture, the differentiated cell body was sub-cultured every week by using McClain tissue chopper (Mickle Engineering, Great Britain), and the medium was replaced every other day. To induce the further differentiation into neuronal cells and glial cells, the collected GM1-NPCs were cultured as attached on the matrigel-coated coverslip in NPCs medium not-containing the growth factor for 3~4 weeks. The nucleotide sequence mutation in GLB1, which is the causing gene of GM1, was investigated using the differentiated GM1-NPCs by the same manner as described in Example <1-1>. As for the control, WT-iPSCs were cultured by the same manner as described above to induce the differentiation of WT-EB and WT-NPCs from WT-iPSCs.

As a result, as shown in FIG. 4, the GM1 originated NPCs maintained the spherical morphology of neurosphere during the suspension culture, and displayed the same c.601C>T mutation in GLB1 gene as GM1 fibroblast cell line and GM1-iPSCs showed (FIG. 4).

<4-2> Differentiation Potency of GM1-iPSCs Originated Embryoid Body (EB)

To investigate the differentiation potency of GM1-iPSCs originated embryoid body (GM1-EB), the expressions of the three germ layer markers such as NESTIN and TUJ1 (ectoderm markers), SOX17 and FOXA2 (endoderm markers), and α-smooth muscle actin (α-SMA) DESMIN (mesoderm markers) were investigated.

Particularly, the GM1-EB differentiated by the same manner as described in Example <4-1> was immunofluorescent-stained to confirm the expression of NESTIN, TUJ1, SOX17, FOXA2, α-SMA, or DESMIN. As the primary antibody for the immunofluorescent staining, anti-NESTIN antibody (1:100; MAB5326, Chemicon, USA), anti-TUJ1 antibody (1:500; PRB-435P, Covance, USA), anti-SOX17 antibody (1:100; MAB1924, R&D Systems, USA), anti-FOXA2 antibody (1:1000; ab40874, Abcam, USA), anti-α-SMA antibody (1:400; A5228, Sigma-Aldrich, USA), or anti-DESMIN antibody (1:50; AB907, Chemicon, USA) was used. To compare the expression level, the cells were treated with 4'6-diamidino-2-phenylindole (DAPI) to stain nuclei.

As a result, as shown in FIG. 15, the GM1 originated, differentiated cells expressed all of those three germ layer marker proteins such as ESTIN, TUJ1, SOX17, FOXA2, α-SMA, and DESMIN, indicating the cells had pluripotency (FIG. 15).

Example 5: Characteristics of GM1-iPSCs Originated NPCs

<5-1> Confirmation of the Neuronal Marker Gene Expression in GM1-iPSCs Originated NPCs To investigate the differentiation of GM1-iPSCs originated NPCs (GM1-NPCs), quantitative real-time PCR (qPCR) was performed, by which the mRNA transcriptional levels of the neuronal marker genes such as NESTIN, NCAM, PAX6, and OTX2, and the pluripotent marker gene REX1 were observed in GM1-fibroblasts, GM1-iPSCs, and GM1-NPCs.

Particularly, GM1-iPSCs were constructed by the same manner as described in Example 2 and the differentiation of GM1-NPCs was induced by the same manner as described in Example <4-1>. Then, RNA was extracted from GM1-fibroblasts, GM1-iPSCs, or GM1-NPCs by using RNAiso Plus (Takara, Japan) or RNeasy mini kit (Qiagen, USA) according to the manufacturer's protocol. Reverse transcription PCR (PT PCR) was performed using 1~2 µg of the extracted RNA as a template with Superscript III (Invitrogen, USA) in order to synthesize cDNA of the cell genome. Upon completion of the RT-PCR, 10 µl of qPCR reaction mixture was prepared by mixing 0.2 μl of the reaction product above, 1 μM oligonucleotide primer, 0.5 μl of FAST SYBR green master mix (Applied Biosystems, USA), and distilled water, which proceeded to qPCR using 7500 Fast Real-time PCR system (Applied Biosystems, USA). The expression of the control GAPDH gene was also confirmed by the same manner as described above to correct the expression level. Based on the expression level of GAPDH mRNA, the fold change of NESTIN, NCAM, PAX6, OTX2, or REX1 mRNA was calculated.

As a result, as shown in FIG. 16, the expressions of the neuronal marker genes such as NESTIN, NCAM, PAX6, and OTX2 were confirmed in WT-NPCs and GM1-NPCs differentiated from WT-iPSCs and GM1-iPSCs. In the meantime, the expression of REX1, the pluripotent marker gene, was significantly decreased (FIG. 16). Also, the expression level of the neuronal marker in GM1-NPCs was lower than that in WT-NPCs, suggesting that the differentiation efficiency of GM1-iPSCs into neuronal cells was low (FIG. 16).

<5-2> Expression of Neuronal Marker Protein in GM1-NPCs and the Cells Differentiated from the Same To confirm whether or not NPCs, neuronal cells, and glial cells were successfully differentiated from GM1-iPSCs, the expressions of the neuronal cell-specific marker proteins NESTIN, MAP2, TUJ1, and S100 were confirmed in the NPCs, neuronal cells, and glial cells differentiated from GM1-iPSCs.

Particularly, the differentiation of GM1-NPCs, and the differentiations of GM1-neuronal cells and GM1-glial cells were induced by the same manner as described in Example <4-1>. Then, immunofluorescent staining was performed by the same manner as described in Example <1-3> to confirm the expressions of NESTIN, MAP2, TUJ1, and S100. As the primary antibody for the immunofluorescent staining, anti-NESTIN antibody was used for NPCs, anti-TUJ1 antibody and anti-MAP2 antibody (1:500; AB5622, Chemicon, USA) were used for neuronal cells, and anti-S100 antibody (1:100; ab52642, Abcam, USA) was used for glial cells. To compare the expression level, the nuclei were stained with 4'6-diamidino-2-phenylindole (DAPI) and compared. As for the control, WT-NPCs, and WT-NPCs originated neuronal cells and glial cells were immunofluorescent-stained under the same conditions as described above in order to examine the expression of the neuronal cell-specific marker protein.

As a result, as shown in FIG. 17, it was confirmed that MAP2 and TUJ1 positive neuronal cells and S100 positive glial cells were differentiated from both WT-NPCs and GM1-NPCs (FIG. 17).

<5-3> Morphological Characteristics of GM1-NPCs

To confirm the morphological characteristics of GM1-NPCs, the morphology of the differentiated neurosphere originated from GM1-NPCs was investigated.

Particularly, the differentiations of GM1-NPCs and GM1-NPCs originated neurosphere were induced by the same manner as described in Example <4-1>. Then, the size and the shape of the neurosphere differentiated from GM1-NPCs were examined by phase-contrast microscopy. As for the control, the size and the shape of the neurosphere differentiated from WT-NPCs were examined and compared with the above.

As a result, as shown in FIG. 18, most of the neurospheres originated from WT-NPCs were in the round shape with clear rim, while those neurospheres originated from GM1-NPCs were not in the round shape and in the average size of approximately 36.28% by that of the control (FIG. 18). Cystic neurosphere was rich in the GM1-iPSCs originated neurosphere. Precisely, the cystic neurosphere yield of WT-neurosphere was 7.31±1.43%, while the cystic neurosphere yield of GM1-neurosphere was at least 40%.

<5-4> Differentiation of Neural Rosettes from GM1

To investigate whether or not neuronal cells were efficiently differentiated from GM1-iPSCs, columnar neuroepithelial cells were prepared. To investigate the formation of neural rosettes which are the important structure for the formation of neuroectoderm, the teratoma was induced with GM1-iPSCs in an immune-deficient mouse, followed by investigation of neural rosette formation in the teratoma.

Particularly, the formation of teratoma was induced from GM1-iPSCs in an immune-deficient mouse by the same manner as described in Example <1-4>. Then, nerve tissue and cartilage tissue were obtained. The mature neuronal cells in GM1-teratoma were observed by H&E staining. The generated teratoma was confirmed by immunocytochemistry using anti-TUJ1 antibody and anti-TH antibody.

As a result, as shown in FIG. 19, in those tissues originated from mesoderm such as cartilage tissue or endoderm, there was no difference between the teratoma originated from WT-iPSCs and the teratoma originated from GM1-iPSCs. On the other hand, the teratoma originated from GM1-iPSCs contained as less neural rosettes as under 1% by the total area, while the teratoma originated from WT-iPSCs contained neural rosettes approximately 9% by the total area, suggesting that the neural rosette formation was not as successful in the teratoma originated from GM1-iPSCs as in the teratoma originated from WT-iPSCs (FIG. 19). In the case of inducing neural rosettes in vitro, the yield of neural rosettes differentiated from GM1-iPSCs was about 13% by the yield produced in WT-iPSCs, suggesting that GM1-iPSCs had defect of neuronal differentiation potency.

Example 6: Molecular Phenotype of GM1 Patient Originated iPSCs and Neuronal Cells Differentiated from the Same <6-1> Expressions of GLB1 Gene and Protein in GM1-iPSCs and GM1-NPCs Differentiated from the Same To confirm whether or not the GM1 patient originated iPSCs and GM1-NPCs differentiated from the same had the same molecular phenotype as that of GM1 patient, as shown in FIG. 20, the expressions of GLB1 gene and protein in GM1-fibroblasts, GM1-iPSCs, and GM1-NPCs were investigated.

Particularly, GM1-iPSCs were prepared by the same manner as described in Example 2 and the differentiation of GM1-NPCs was induced by the same manner as described in Example <4-1>. Then, qPCR was performed with -fibroblasts, GM1-iPSCs, and GM1-NPCs by the same manner as described in Example <4-2> to confirm the expression level of GLB1 mRNA.

The induced GM1-fibrablasts, GM1-iPSCs, or GM1-NPCs were obtained, which were lysed in RIPA buffer, followed by centrifugation at 4° C. to eliminate the cell debris. Then, 20~30 μg of the cell lysate was electrophoresed on 4~15% gel (Bio-Rad, USA) to separate protein. The obtained protein was transferred onto PVDF membrane (Bio-Rad, USA), followed by Western blotting using anti-GLB1 antibody (1:500; AF6464, R&D systems, USA). As for the control to correct the color development, GAPDH was stained by treating anti-GAPDH antibody.

As a result, as shown in FIG. 21, the levels of GLB1 (β-gal) mRNA and protein were all increased in the GM1 originated cells, compared with in the normal cells, and the expression was most increased in GM1-NPCs (FIG. 21).

<6-2> β-Gal Activity in GM1-iPSCs and GM1-NPSc Differentiated from the Same

Even though GLB1 mRNA and protein were upregulated in GM1-iPSCs and GM1-NPCs, β-gal activity was low in GM1 patient. Therefore, X-gal staining was performed to confirm the β-gal activity in GM1-iPSCs and GM1-NPCs.

Particularly, GM1-iPSCs were constructed by the same manner as described in Example 2, and the differentiation of GM1-NPCs was induced therefrom by the same manner as described in Example <4-1>. PBS was replaced with a low pH buffer at pH 4.5 containing 50 mM citrate and 150 mM NaCl. X-gal staining was performed using β-gal staining kit (INtRon Biotechnology, Korea) according to the manufacturer's protocol. When blue color was shown, X-gal staining was terminated. The culture time was 4 hours~overnight according to the cell types.

As a result, as shown in FIG. 22, at least 90% of normal fibroblasts, WT-iPSCs, and WT-NPCs were stained by X-gal, while GM-fibroblasts, GM1-iPSCs, and GM1-NPCs lost β-gal activity, confirmed by scattered blue color resulted from X-gal staining (FIG. 22).

<6-3> Accumulation of GM1 Ganglioside in GM1-iPSCs and GM1-NPCs

To confirm whether or not the accumulation of GM1 ganglioside was caused by the decrease of β-gal activity in GM1 patient, the accumulation of GM1 ganglioside and lysosome was investigated in GM1-iPSCs and GM1-NPCs.

Particularly, GM1-iPSCs were constructed by the same manner as described in Example 2, and the differentiation of GM1-NPCs was induced therefrom by the same manner as described in Example <4-1>. Then, GM1 ganglioside in GM1-fibroblasts and GM1-iPSCs was immunofluorescent-stained by the same manner as described in Example <3-3>. The primary antibody used herein was anti-GM1 antibody (1:50; ab23943, Abcam, USA). To measure the content of lysosome in GM1-fibroblasts and GM1-NPCs, the culture medium was treated with LysoTracker Red DND-99 (1:20000; Invitrogen, USA), followed by reaction at 37° C. for 30 minutes. Then, intracellular lysosome was observed. The accumulation of GM1 ganglioside and lysosome in the control (WT-fibroblasts, WT-iPSCs, and WT-NPCs) was also measured by the same manner as described above.

As a result, as shown in FIG. 23, the expression of GM1 ganglioside in the wild-type cells was very low, but the accumulation of GM1 ganglioside in GM1-fibroblasts and GM1-iPSCs was high (FIG. 23). The lysosome content in GM1-NPCs was also high, compared with that in WT-NPCs, suggesting that the accumulation of lysosome was induced by the accumulation of GM1 ganglioside (FIG. 23).

Example 7: Investigation of Transcripts of GM1-iPSCs and Neuronal Cells Differentiated from the Same <7-1> Gene Expression Pattern in GM1-iPSCs and GM1-NPCs To understand genetic cause of GM1, gene expression patterns in GM1-iPSCs and GM1-NPCs were investigated.

Particularly, GM1-iPSCs were constructed by the same manner as described in Example 2, and the differentiation of GM1-NPCs was induced therefrom by the same manner as described in Example <4-1>. Then, GM1-fibroblasts, GM1-iPSCs, and GM1-NPCs were obtained. Microarray was performed by using Low RNA input linear amplification kit, cRNA cleanup module, and Whole Human Genome Microarray 4×44K (Agilent Technology, USA) according to the manufacturer's protocol. The obtained microarray images were revised as signals corresponding to WT-fibroblasts, WT-iPSCs, and WT-NPCs. The revised value was used to make heatmap by using MeV program and the gene that did not show any change in expression pattern (the change less than double) was discarded.

As a result, as shown in FIG. 24, the gene expression pattern change was most significant in GM1-NPCs, compared with normal cells, suggesting that GM1-NPCs were the most proper model for the analysis of genetic change in GM1 (FIG. 24).

Also, as shown in FIG. 25, the expression of B4GALNT1 playing an important role in GM1 ganglioside synthesis as a GM2 synthase in lysosomal sphingolipid metabolic pathway was reduced in GM1 cells. In the meantime, the expression of GLB1 enzyme playing a role in eliminating GM1 ganglioside was increased. Therefore, the gene expression to compensate the decrease of β-gal activity in GM1-NPCs, to increase sphingolipid metabolism, and to inhibit the increase of GM1 ganglioside accumulation was confirmed (FIG. 25).

<7-2> Gene Expression Pattern in GM1 Mouse Model and GM1-NPCs

To investigate whether or not the GM1-iPSCs originated GM1-NPCs were appropriate as the GM1 model, it was investigated whether or not the unfolded protein response (UPR) that was reported previously to be displayed in GM1 mouse model (β-gal$^{-/-}$) was observed in GM1-NPCs (Tessitore A, et al. *Molecular cell* 15, 753~766, 2004).

Particularly, GM1-iPSCs were constructed by the same manner as described in Example 2, and the differentiation of GM1-NPCs was induced therefrom by the same manner as described in Example <4-1>. Then, GM1-fibroblasts, GM1-iPSCs, and GM1-NPCs were obtained, followed by microarray as described in Example <7-1> to examine the gene expression pattern in normal cells and the obtained cells. The gene displayed any change in expression level was selected. The mRNA expression levels of CHOP, BiP, XBP1, PD1A4, and CALR, which were the UPR genes that had been reported earlier to be up-regulated in GM1 model, were compared by qPCR according to the same manner as described in Example <5-1> with the relative mRNA expression levels in WT-NPCs and GM1-NPCs.

As a result, as shown in FIG. 26, similar up-regulation of the URP gene to such level as reported previously was observed in GM1-NPCs. That is, the change of expression pattern was similar to that of GM1 mouse model but the mRNA expression in GM1-fibroblasts and GM1-iPSCs was not significantly changed (FIG. 26).

Example 8: Investigation of the Activation of Immunometabolic Pathway in GM1-NPCs <8-1> Metabolic Pathway Specifically Expressed in GM1-NPCs To confirm any metabolic pathway that could affect the symptoms of GM1 patient, the metabolic pathway that was specifically up-regulated in GM1-NPCs was investigated.

Particularly, GM1-iPSCs were constructed by the same manner as described in Example 2, and the differentiation of GM1-NPCs was induced therefrom by the same manner as described in Example <4-1>. Then, GM1-fibroblasts, GM1-iPSCs, and GM1-NPCs were obtained, followed by microarray as described in Example <7-1> to examine the gene expression pattern in normal cells and the obtained cells. The gene displayed any change in expression level was selected. The selected gene was analyzed by KEGG using DAVID Bioinformatics Resource (http://david.abcc.ncifcrf- .gov). Interactive pathway analysis (IPA) was performed by using Ingenuity Systems (EBIOGEN Inc.). The mRNA expression levels of CHOP, BiP, XBP1, PD1A4, and CALR, which were the UPR genes that had been reported earlier to be up-regulated in GM1 model, were compared by qPCR according to the same manner as described in Example <5-1> with the relative mRNA expression levels in WT-NPCs and GM1-NPCs.

Figure 27A:
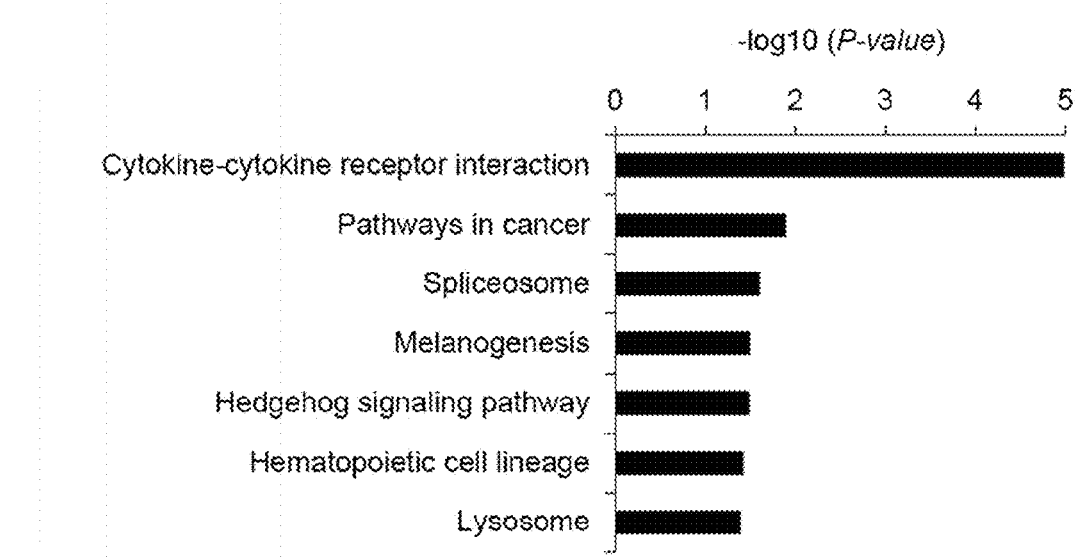
FIGS. 27A-27B present the GM1-NPCs specific expression pathway.
Figure 27B:
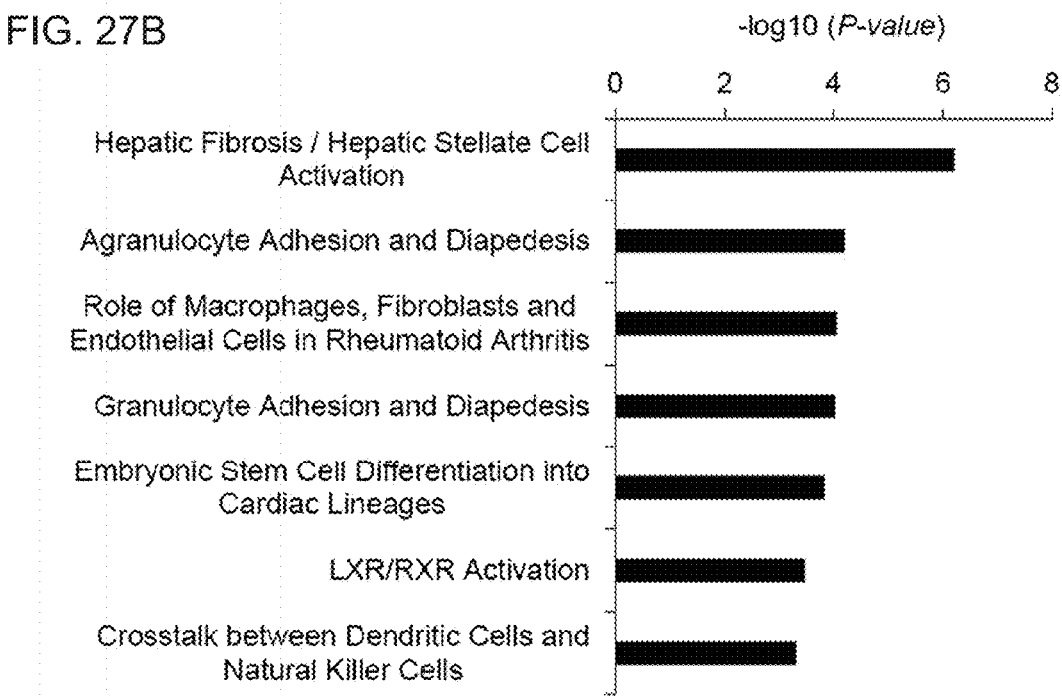

As a result, as shown in FIG. 27, various metabolic pathways were up-regulated in GM1-NPCs. In particular, it was confirmed that cytokine-cytokine receptor interaction was increased (FIG. 27a). In addition, immune response related metabolic pathways were significantly up-regulated, suggesting that immune response was closely related to neuropathic symptoms of GM1 (FIG. 27b).

<8-2> Expression of Inflammasome Related Metabolic Pathway in GM1-NPCs

To investigate whether or not the inflammation response was increased according to the up-regulation of inflammation related metabolic pathway in GM1-NPCs, the expression pattern of the gene involved in inflammasome in GM1-NPCs was investigated.

Particularly, GM1-iPSCs were constructed by the same manner as described in Example 2, and the differentiation of GM1-NPCs was induced therefrom by the same manner as described in Example <4-1>. Then, GM1-fibroblasts, GM1-iPSCs, and GM1-NPCs were obtained, followed by microarray as described in Example <7-1> to investigate the up- or down-regulation of the gene involved in inflammasome. The gene whose expression pattern was significantly changed, compared with that in WT-NPCs was selected, followed by qPCR according to the same manner as described in Example <5-1> in order to compare the relative mRNA expression level in WT-NPCs and GM1-NPCs.

As a result, as shown in FIG. 28 and FIG. 29, the expressions of most inflammasome factors were very low in WT-NPCs, while the inflammasome related metabolic pathway was highly activated in GM1-NPCs (FIG. 28). When the relative mRNA expression was quantified, the expression of apoptotic caspase in GM1-NPCs was similar to that in WT-NPCs, while the expressions of inflammatory caspase, inflammatory interleukin, IL1β downstream genes, and inflammation related metabolic factors were significantly increased in GM1-NPCs, compared with those in WT-NPCs (FIG. 29).

Example 9: Alleviation of Neural Damage by the Inhibition of Inflammasome in GM1-NPCs <9-1> Recovery of GM1-NPCs Morphology by the Inhibition of Inflammasome To investigate the recovery of neural damage caused by the increased activation of inflammasome related metabolic pathway in GM1, GM1-NPCs were treated with the inflammasome inhibitors IL1β antagonist (rhIL1RA) and caspase-1 inhibitor (Z-YVAD-FMK), and then the morphology of GM1-NPCs was investigated.

Particularly, the differentiation of GM1-NPCs was induced by the same manner as described in Example <4-1>. Then, the induced GM1-NPCs were cultured in the culture medium respectively treated with 1 μg/ml rhIL1RA (R&D Systems, USA) or 10 μM Z-YVAD-FMK (Merck Millipore, Germany) in order to inhibit inflammasome therein. 2~4 weeks later, the cultured GM1-NPCs originated neurosphere was obtained. The morphology of neurosphere was observed by phase-contrast microscopy.

Figure 30A:
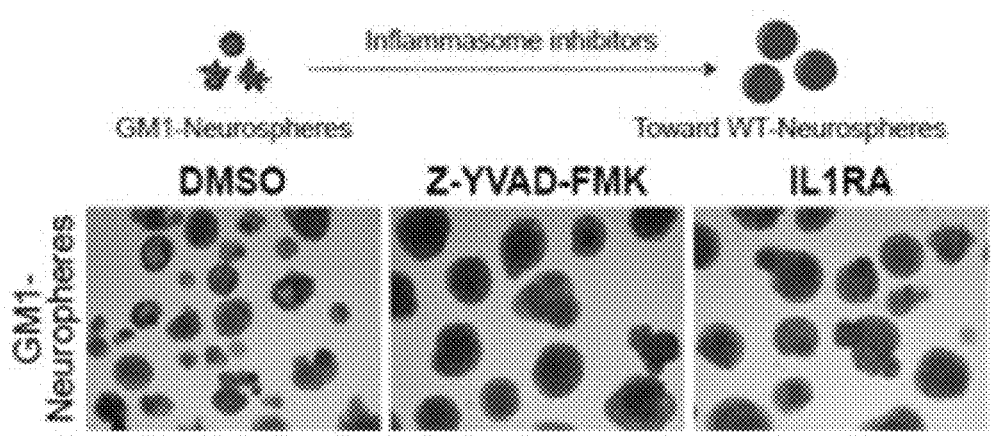
FIGS. 30A-30C present the morphological changes of the GM1-neurosphere differentiated by treating an inflammasome inhibitor.
Figure 30B:
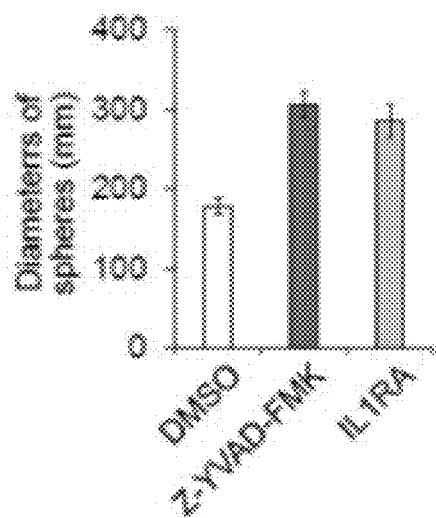
Figure 30C:
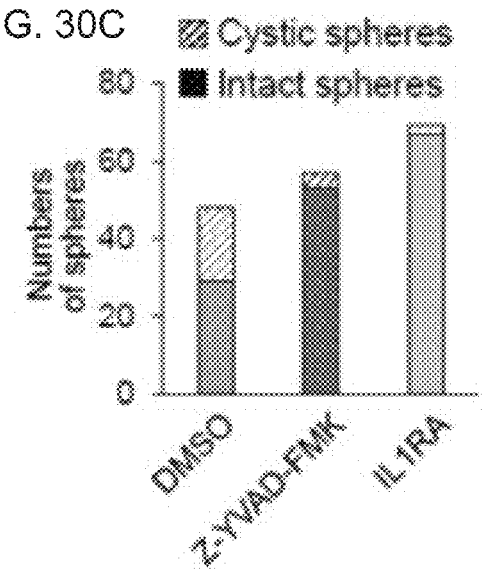

As a result, as shown in FIG. 30, when an inflammasome inhibitor was treated thereto, the abnormal morphology of GM1-neurosphere was recovered back to the normal shape (FIG. 30a). As the neurosphere morphology was recovered, the neurosphere diameter was increased (FIG. 30b). The formation of cystic neurosphere was significantly reduced, and accordingly the number of normal neurosphere was increased (FIG. 30c).

<9-2> Changes of Gene Expression Pattern in GM1-NPCs According to the Inhibition of Inflammasome To investigate whether or not the neural damage could be alleviated according to the increase of the activation of inflammasome related metabolic pathway in GM1, the gene expression pattern in GM1-NPCs treated with the inflammasome inhibitor was investigated.

Particularly, GM1-NPCs were differentiated according to the method described in Example <4-1>, and then treated with rhIL1RA or Z-YVAD-FMK by the same manner as described in Example <9-1>. Microarray was performed by the same manner as described in Example <7-1> in order to investigate the up- or down-regulation of the gene involved in inflammasome. The gene whose expression pattern was significantly changed, compared with that in WT-NPCs was selected, followed by qPCR according to the same manner as described in Example <5-1> in order to compare the relative mRNA expression level in WT-NPCs and GM1-NPCs. WT-NPC was used as the normal control. As for the negative control, GM1-NPCs were treated with DMSO instead of rhIL1RA or Z-YVAD-FMK. The expression pattern (either up- or down regulation) and the mRNA expression level were investigated by the same manner as described above.

As a result, as shown in FIG. 31~FIG. 34, the gene expression pattern in GM1-NPCs was changed by the treatment of the inflammasome inhibitor, and therefore the expressions of inflammasome related factors which had been increased in GM1-NPCs were significantly reduced (FIG. 34). In the GM1-NPCs treated with Z-YVAD-FMK (caspase-1 inhibitor), 9.3% of total 27,375 oligo probe pairs displayed the changed expression pattern (FIG. 31). Most of those genes demonstrating changes in their expression patterns had the tendency to recover their gene expression patterns changed by GM1 mediated neural damage back to the normal pattern (FIG. 31). For example, the expression of GLB1, the GM1 causing protein, was 47% reduced, compared with that in GM1-NPCs, and the reduced B4GALNT expression was increased by 2.6 fold (FIG. 32). When inflammasome was inhibited by the treatment of rhIL1RA, 3.6% of the genes displayed the changed expression pattern, but they also had the tendency to recover the abnormal gene expression in GM1 cells to the normal expression pattern (FIG. 33).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treatment of GM1 gangliosidosis comprising:
selecting a subject with GM1 gangliosidosis; and
administering a pharmaceutically effective dose of Z-YVAD-FMK (methyl (3S)-3-[(2S)-2-[(2S)-2-(2-{[(benzyloxy)carbonyl]amino}-3-(4-hydroxyphenyl) propanamido)-3-methylbutanamido]propanamido]-5-fluoro-4-oxopentanoate) to the subject, thereby treating the GM1 gangliosidosis.

2. The method for treatment of GM1 gangliosidosis according to claim 1, wherein the Z-YVAD-FMK recovers GM1 patient-specific neuronal progenitor cell morphology to a normal shape.

3. A method for altering expression of neuronal genes in neuronal cells in a subject with GM1 gangliosidosis, comprising:
   selecting a subject with GM1 gangliosidosis; and
   administering a pharmaceutically effective dose of Z-YVAD-FMK (methyl (3S)-3-[(2S)-2-[(2S)-2-(2-{[(benzyloxy)car bonyl]amino}-3-(4-hydroxyphenyl)propanamido)-3-methylbutanamido]propanamido]-5-fluoro-4-oxopentanoate) to the subject, thereby altering the expression of neuronal marker genes in neuronal cells in the subject with GM1 gangliosidosis.

4. The method of claim 3, wherein the neuronal genes comprise a gene encoding GLB1 and a gene encoding B4GALNT.

5. The method of claim 4, wherein expression of the gene encoding GLB1 is reduced and expression of the gene encoding B4GALNT is increased by the pharmaceutically effective dose of Z-YVAD-FMK (methyl (3S)-3-[(2S)-2-[(2S)-2-(2-{[(benzyloxy)car bonyl]amino}-3-(4-hydroxyphenyl)propanamido)-3-methylbutanamido]propanamido]-5-fluoro-4-oxopentanoate).

6. The method of claim 1, wherein treating the GM1 gangliosidosis comprises altering expression of neuronal genes in neuronal cells in the subject.

* * * * *

SEQUENCE LISTING

<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Tyr Val Ala Asp
1

<210> SEQ ID NO 2
<211> LENGTH: 153
<212> TYPE: PRT
<213> ORGANISM: homo sapiens

<400> SEQUENCE: 2

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 3
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 3
ccgcggccgc atgccggggt tcctggttcg cat                                33

<210> SEQ ID NO 4
<211> LENGTH: 29
<212> TYPE: DNA
<213> ORGANISM: artificial sequence
<220> FEATURE:
<223> OTHER INFORMATION: oligonucleotide primer

<400> SEQUENCE: 4
ggctcgagta catggtccag ccatgaatc                                     29

<210> SEQ ID NO 5

```
<211> LENGTH: 20
<212> TYPE: DNA
<213> ORGANISM: artificial sequence
<220> FEATURE:
<223> OTHER INFORMATION: oligonucleotide primer

<400> SEQUENCE: 5
ctatagccgg gactccttcc                                                    20

<210> SEQ ID NO 6
<211> LENGTH: 20
<212> TYPE: DNA
<213> ORGANISM: artificial sequence
<220> FEATURE:
<223> OTHER INFORMATION: oligonucleotide primer

<400> SEQUENCE: 6
agttccaggg cacatacgtc                                                    20

<210> SEQ ID NO 7
<211> LENGTH: 20
<212> TYPE: DNA
<213> ORGANISM: artificial sequence
<220> FEATURE:
<223> OTHER INFORMATION: oligonucleotide primer

<400> SEQUENCE: 7
cccagaggga cacagaatgt                                                    20

<210> SEQ ID NO 8
<211> LENGTH: 20
<212> TYPE: DNA
<213> ORGANISM: artificial sequence
<220> FEATURE:
<223> OTHER INFORMATION: oligonucleotide primer

<400> SEQUENCE: 8
cctgcagaag cgctttcgcc                                                    20

<210> SEQ ID NO 9
<211> LENGTH: 22
<212> TYPE: DNA
<213> ORGANISM: artificial sequence
<220> FEATURE:
<223> OTHER INFORMATION: oligonucleotide primer

<400> SEQUENCE: 9
cgagcatatg ttgctgtgga tg                                                 22

<210> SEQ ID NO 10
<211> LENGTH: 22
<212> TYPE: DNA
<213> ORGANISM: artificial sequence
<220> FEATURE:
<223> OTHER INFORMATION: oligonucleotide primer

<400> SEQUENCE: 10
gccaggccgt gggtccttag tc                                                 22
```